(12) United States Patent
Kouda et al.

(10) Patent No.: US 7,748,275 B2
(45) Date of Patent: Jul. 6, 2010

(54) PRESSURE SENSOR FOR EXTRACORPOREAL CIRCULATING CIRCUIT

(75) Inventors: Masaaki Kouda, Tokyo (JP); Kengo Kobayashi, Tokyo (JP)

(73) Assignee: Asahi Kasei Kuraray Medical Co., Ltd., Tokyo (JP)

(*) Notice: Subject to any disclaimer, the term of this patent is extended or adjusted under 35 U.S.C. 154(b) by 106 days.

(21) Appl. No.: 12/282,072

(22) PCT Filed: Apr. 18, 2007

(86) PCT No.: PCT/JP2007/058446
§ 371 (c)(1),
(2), (4) Date: Sep. 8, 2008

(87) PCT Pub. No.: WO2007/123156
PCT Pub. Date: Nov. 1, 2007

(65) Prior Publication Data
US 2009/0071258 A1  Mar. 19, 2009

(30) Foreign Application Priority Data

Apr. 19, 2006 (JP) ............... 2006-115852
Aug. 24, 2006 (JP) ............... 2006-228483
Apr. 10, 2007 (JP) ............... 2007-102486
Apr. 10, 2007 (JP) ............... 2007-102487

(51) Int. Cl.
*G01L 7/00* (2006.01)
(52) U.S. Cl. ............... 73/714; 604/7
(58) Field of Classification Search ............... None
See application file for complete search history.

(56) References Cited

U.S. PATENT DOCUMENTS 3,981,197 A * 9/1976 Lieber et al. ............... 73/727

(Continued)

FOREIGN PATENT DOCUMENTS

DE  4219888  1/1994

(Continued)

OTHER PUBLICATIONS

English language Abstract of DE 4219888, Jan. 13, 1994.

(Continued)

*Primary Examiner*—Lisa M Caputo
*Assistant Examiner*—Jermaine Jenkins
(74) *Attorney, Agent, or Firm*—Greenblum & Bernstein P.L.C.

(57) ABSTRACT

A pressure sensor for an extracorporeal circulating circuit includes a liquid chamber, a pressure measuring means, and a liquid flow path. The liquid chamber includes a reference surface not deformed by a pressure in the extracorporeal circulating circuit, a deforming surface disposed separated from the reference surface and deformed at least partially by a pressure in the extracorporeal circulating circuit, a first connection surface that joins the deforming surface with the reference surface to form a closed liquid-tight space inside them and is not deformed by a pressure in the extracorporeal circulating circuit, a liquid inflowing port provided in the side surface of the first connection surface, and a liquid outflowing port disposed away by ½ to less than one round from the inflowing port in the flowing direction of liquid introduced along the inner periphery of the side surface of the first connection surface. The pressure measuring means measures the deformation amount of the deforming surface, and is disposed outside the liquid chamber; and the liquid flow path is liquid-tightly connected with the liquid inflowing port so that liquid to be introduced into the liquid chamber flows in along the inner periphery of the side surface of the first connection surface.

19 Claims, 19 Drawing Sheets

U.S. PATENT DOCUMENTS

| | | | |
|---|---|---|---|
| 4,185,641 A | | 1/1980 | Minior et al. |
| 4,574,811 A | | 3/1986 | Stephens |
| 5,554,113 A | * | 9/1996 | Novak et al. .................. 604/30 |
| 5,722,399 A | | 3/1998 | Chevallet et al. |
| 6,649,046 B2 | * | 11/2003 | Chevallet .................... 210/90 |
| 6,880,404 B2 | * | 4/2005 | Uberreiter ................... 73/706 |
| 6,964,646 B1 | * | 11/2005 | Biesel .......................... 604/7 |
| 6,976,964 B2 | * | 12/2005 | Chevallet et al. ............ 600/486 |
| 7,069,788 B2 | * | 7/2006 | Teugels ....................... 73/706 |
| 7,181,975 B1 | * | 2/2007 | Bradley et al. ............... 73/724 |
| 7,516,665 B2 | * | 4/2009 | Teugels ....................... 73/706 |
| 2002/0073782 A1 | * | 6/2002 | Chevallet et al. ............. 73/700 |
| 2004/0050168 A1 | * | 3/2004 | Uberreiter ................... 73/706 |

FOREIGN PATENT DOCUMENTS

| | | | |
|---|---|---|---|
| EP | | 0208955 | 1/1987 |
| JP | | 62-19151 | 1/1987 |
| JP | | 62-211043 | 9/1987 |
| JP | | 2-1219 | 1/1990 |
| JP | | 02102638 A * | 4/1990 |
| JP | | 8-117332 | 5/1996 |
| JP | | 9-24026 | 1/1997 |
| JP | | 2002-282355 | 10/2002 |

OTHER PUBLICATIONS

English language Abstract of JP 9-24026, Jan. 28, 1997.
English language Abstract of JP 2002-282355, Oct. 2, 2002.
English language Abstract of JP 2-1219, Jan. 5, 1990.
English language Abstract of JP 62-19151, Jan. 27, 1987.
English language Abstract of JP 8-117332, May 14, 1996.
English language Abstract of EP 0208955, Jan. 21, 1987.

* cited by examiner

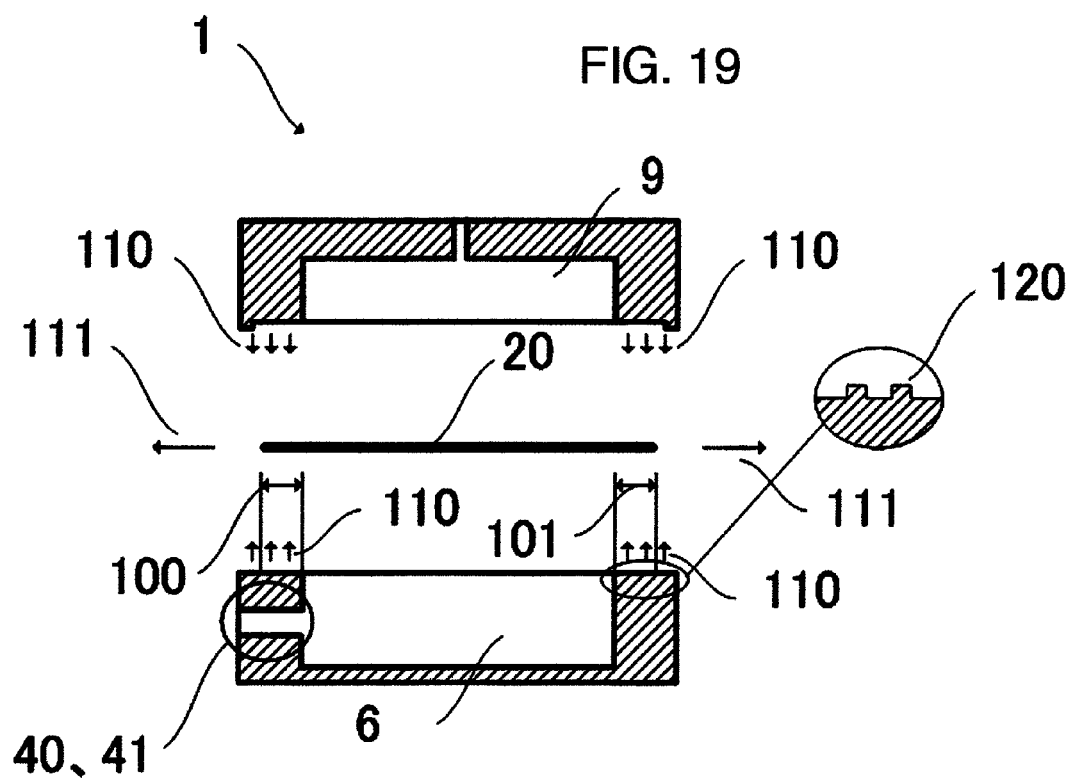
FIG. 19
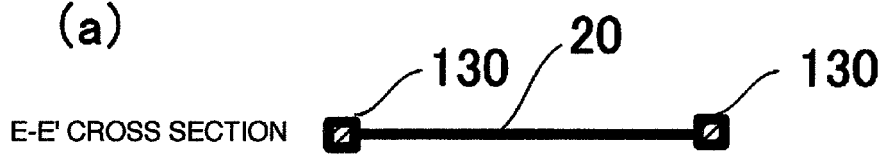
FIG. 20
(a) E-E' CROSS SECTION
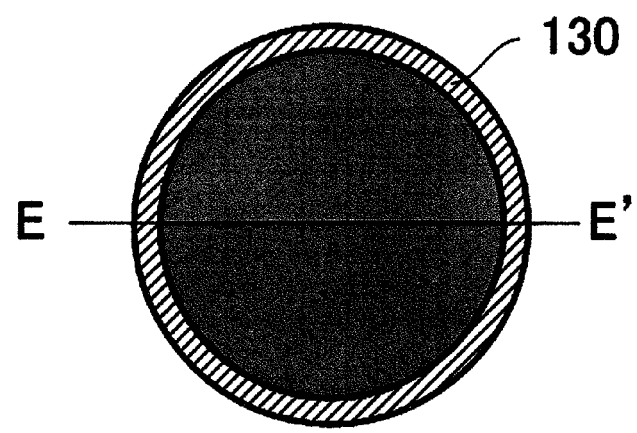
(b)

(A)

(B)

US 7,748,275 B2

PRESSURE SENSOR FOR EXTRACORPOREAL CIRCULATING CIRCUIT

TECHNICAL FIELD

The present invention relates to a pressure sensor for measuring a pressure in an extracorporeal circulating circuit which causes a liquid, specifically body fluid or medicinal solution to flow therein.

BACKGROUND ART

In an extracorporeal circulation therapy in which blood is pulled out of the body of a patient for an extracorporeal treatment by a blood processing apparatus and the blood is returned into the body after the treatment, usually, a pressure sensor is provided to measure a pressure in the extracorporeal circulating circuit. As an example of the means for measuring a pressure in an extracorporeal circulating circuit, Patent Document 1 describes a pressure measuring method using a drip chamber which is commonly used in an extracorporeal circulation therapy.

FIG. 33 is a schematic configuration view showing an example of a pressure measuring method using a drip chamber. As shown in FIG. 33, a drip chamber 2 is disposed in the middle of a liquid flow path 8, and is configured with a branch tube 500 branched from the top of the drip chamber 2 and a liquid chamber pressure measuring means 61 at the end of the branch tube 500. In a pressure measuring method using such drip chamber as shown in FIG. 33, a certain volume of the drip chamber 2, e.g. a half of the volume of the drip chamber 2, body fluid or medicinal solution is stored in the drip chamber 2 with the remaining half of the volume being filled with a layer of air to perform an extracorporeal circulation therapy. The means for measuring pressure of an air chamber measures a pressure in the liquid flow path 8 without a directly contact with the body fluid or medicinal solution due to the air layer.

However, the drip chamber 2 has an inner diameter which provides a large contact area between the body fluid or medicinal solution and the air, and further provides a large volume of the body fluid or medicinal solution for storage. Thus, it takes a long time to exchange the stored liquid with a liquid to be newly introduced, which may cause retention or coagulation of the body fluid or medicinal solution.

As an example of a pressure sensor to solve the above problem, Patent Document 2 describes a pressure measuring method for measuring a pressure in a liquid flow path via a deformable plane (a deformable portion which is deformed by a pressure in an extracorporeal circulating circuit) as a pressure measuring method to avoid the contact between body fluid or medicinal solution and air.

FIG. 34 is a schematic view showing an example of a pressure measuring method for measuring a pressure in an extracorporeal circulating circuit via a deformable plane. As shown in FIG. 34, a pressure sensor 3 in the prior art is disposed on the way to a liquid flow path 8, and measures a pressure in a liquid chamber 6 by detecting a deformation quantity of a deformable plane 20 which is at least partially deformed by a pressure in the liquid chamber. In FIG. 34, the elements having the same function as those in FIG. 33 are given by the same reference numerals as those in FIG. 33.

In the configuration of the pressure measuring method shown in FIG. 34, the pressure sensor 3 in the prior art includes a liquid flow inlet 40 and a liquid flow outlet 41 which are substantially located in-line. When a liquid is introduced in the liquid flow inlet 40 to be flown into the liquid chamber 6, the flow path is suddenly widened at the exit of the liquid flow inlet 40, and therefore the convection is generated at the liquid flow inlet 40 to cause the liquid flow stagnates. As a result, since the body fluid or medicinal solution remains at a certain position, coagulation of the body fluid may occur.

In the case of a low flow rate, no turbulence is generated in the flow in the liquid chamber 6. However, in this case, since the introduced liquid goes to the liquid flow outlet 41 which is substantially in-line with regard to the liquid flow inlet 40, the exchange of the liquids in the liquid chamber 6 is not promoted, which may result in coagulation of body fluid therein. In addition, the pressure in the pressure sensor 3 in the prior art as shown in FIG. 34 is highly variable, and in the case of a negative pressure, the deformable plane 20 closely contacts a wall surface of the liquid chamber 6, and therefore the liquid flow outlet or the liquid flow inlet may be blocked. In this case, since the flow of body fluid is stopped, coagulation of the body fluid may be caused.

Also, because the deformable plane 20 has a corrugated shape, the air chamber 9 has to have a sufficient depth (which at least has size of not less than corrugated shape) to a certain degree in the direction perpendicular to the direction in which the deformable plane 20 is disposed to give a margin for the width of the corrugated shape in the direction of its convexo-concave configuration. This does not allow the air chamber 9 to have a smaller volume. Thus, in measuring a negative pressure, the deformation quantity of the deformable plane 20 in the direction toward the liquid chamber 6 is increased, which eventually increases the volume of the liquid chamber 6 and easily causes the above described stagnation.

Furthermore, the deformable plane 20 in the pressure sensor 3 in the prior art as shown in FIG. 34 may be damaged due to the soft material thereof. In case of damage of the deformable plane, the operation is just like the pressure measuring method using the drip chamber shown in FIG. 33, and cannot avoid the above described problems of coagulation due to the contact between the air and the body fluid or medicinal solution.

Moreover, in the pressure sensor 3 in the prior art as shown in FIG. 34, when the deformable plane 20 is deformed, the pressure in the air chamber 9 changes in correlation with the pressure in the liquid chamber 6. This causes the differences between the pressure characteristics obtained in the case where a pressure is measured via air and in the case where a pressure is measured via the deformable plane, thereby resulting in a problem that no pressure can be correctly measured.

In addition, the pressure sensor 3 in the prior art as shown in FIG. 34 is a disposable product which can be discarded after use, and this requires the connection between a pressure sensor and a pressure measuring means every time the pressure sensor is used. Therefore, if there is any incomplete connection, the leakage between the pressure sensor and the pressure measuring means is caused, thereby making it impossible to correctly measure a pressure therein. Since the leakage provides the air chamber side with an infinite volume, the deformable plane 20 is significantly deformed toward the liquid chamber when the liquid flow path 8 has a negative pressure. As a result, the deformable plane 20 blocks the liquid flow inlet 40 or liquid flow outlet 41, the flow of body fluid or medicinal solution is stopped, and therefore eventually may cause coagulation of the body fluid.

Patent Document 3 describes a pressure sensor for stably measuring a pressure by automatically changing the volume of air on an air chamber 9 side in conjunction with the pressure on a liquid chamber 6 side, so as to control a position of the deformable plane 20.

FIG. 35 is a schematic view showing an example of the configurations of a hydraulic measuring apparatus. As shown in FIG. 35, the pressure sensor 3 in the prior art is configured with, in addition to those of the pressure sensor shown in FIG. 34, a communication section 51 for controlling the volume of air in the air chamber 9, a pump 400 disposed on the communication section 51, a valve 401, air chamber pressure measuring means 60, and second pressure measuring means 62. In FIG. 35, the elements having the same function as those in FIG. 34 are designated by the same reference numerals as those in FIG. 34.

However, the hydraulic measuring apparatus shown in FIG. 35 needs to have a pump, a valve, and separate pressure measuring means mounted thereto, in addition to a pressure sensor which measures a pressure, which inevitably makes the configuration of the apparatus complicated and in turn causes an increased cost of the apparatus. Furthermore, in order to perform a stable pressure measurement, the volume of air in the air chamber should be strictly controlled, which causes the problem that the control requires tremendous accuracy.

Patent Document 1: JP-A-2002-282355
Patent Document 2: JP-A-09-024026
Patent Document 3: JP-A-08-117332

DISCLOSURE OF THE INVENTION

Problem to be solved by the Invention

The present invention was made in view of the above described problems in the prior art, and one object of the present invention is to provide a pressure sensor for measuring a pressure in an extracorporeal circulating circuit without a contacting air wherein the pressure sensor is configured so that any retention of body fluid or medicinal solution is hardly caused therein and no coagulation of the body fluid is generated therein due to flow factors of the body fluid or medicinal solution.

Another object of the present invention is to provide a pressure sensor for measuring a pressure in an extracorporeal circulating circuit without contacting a liquid to with air wherein the pressure sensor can measure a pressure even when the pressure is changing, does not require an increase of the volumes of an air chamber and a liquid chamber, and can detect pressure with small measurement error using one type of pressure sensor without controlling of the volume of air on the air chamber side.

Another object of the present invention is to provide a pressure sensor for measuring a pressure in an extracorporeal circulating circuit without contacting air wherein the pressure sensor includes a means for detecting damage of a deformable plane therein.

Further another object of the present invention is to provide a pressure sensor for measuring a pressure in an extracorporeal circulating circuit without contacting air wherein the pressure sensor includes a means for detecting the attachment of a casing of the pressure sensor to an attachment surface.

Means for Solving the Problem

In order to solve the above problems, a pressure sensor according to the present invention includes the following configurations:

(a) a pressure sensor for an extracorporeal circulating circuit including: a liquid chamber, a pressure measuring means, and a liquid flow path; wherein the liquid chamber is provided with a reference plane which is not deformed by a pressure in the extracorporeal circulating circuit, a deformable plane which is disposed separately from the reference plane and is at least partially deformed by the pressure in the extracorporeal circulating circuit, a first connecting plane which connects the deformable plane with the reference plane to form a closed liquid-tight space therein and is not deformed by the pressure in the extracorporeal circulating circuit, a liquid flow inlet provided in a side surface of the first connecting plane, and a liquid flow outlet which is disposed at a position separated from the liquid flow inlet by a distance from more than one half to less than one of the inner circumference in the direction of a flow of a liquid wherein the liquid is introduced along an inner circumference of side surfaces of the first connecting plane; wherein the pressure measuring means is disposed outside of the liquid chamber for measuring a deformation quantity of the deformable plane; and wherein the liquid flow path is connected to the liquid flow inlet in a liquid tight manner so that the liquid which is introduced into the liquid chamber flows along the inner circumference of side surfaces of the first connecting plane;

(b) the pressure sensor for an extracorporeal circulating circuit according to (a), further including a baffle plate which is disposed near the first connecting plane to disturb the flow of the liquid;

(c) the pressure sensor for an extracorporeal circulating circuit according to (a) or (b), further including an air chamber, wherein the air chamber has an opposing plane which is not deformed by a pressure and is disposed separately from the deformable plane so that the deformable plane is positioned between the reference plane and the opposing plane, a second connecting plane which is not deformed by a pressure and connects the opposing plane with the deformable plane to form a closed air-tight space therein, and an air inlet/outlet which is provided in a side surface of the second connecting plane or the opposing plane, and wherein the pressure measuring means is an air chamber pressure measuring means which is connected to the air inlet/outlet of the air chamber via a communication section;

(d) the pressure sensor for an extracorporeal circulating circuit according to (c), wherein on the assumption that $V_A$ is volume of the air chamber in the initial state, $P_A$ is pressure in the air chamber in the initial state (where $-200$ mmHg$<P_A<200$ mmHg), $V_L$ is volume of the liquid chamber in the initial state, $V_T$ is volume of the communication section, $P_{MIN}$ is the minimum measurable pressure of the pressure sensor (where $-600$ mmHg$<P_{MIN}<-200$ mmHg), $P_{MAX}$ is the maximum measurable pressure (where $200$ mmHg$<P_{MAX}<600$ mmHg), and $P_0$ is atmospheric pressure, $V_A$, $V_L$, and $V_T$ are set to satisfy the following Expressions (1) and (2) (where $P_A$, $P_{MIN}$, $P_{MAX}$ are expressed as gage pressure, and $P_0$ is expressed as absolute pressure), $$\{(P_{MAX}+P_0)\div(P_A+P_0)-1\}\times V_T<V_A \quad (1)$$

$$\{(P_A+P_0)\div(P_{MIN}+P_0)-1\}\times(V_A+V_T)<V_L<10\text{ mL} \quad (2)$$

and the deformable plane has a flat plate shape when the liquid chamber and the air chamber have a pressure $P_0$;

(e) the pressure sensor for an extracorporeal circulating circuit according to (d) wherein the deformable plane is sandwiched between two containers of the air chamber and the liquid chamber to be mechanically sealed at the peripheral portion thereof; and on the assumption that L is width of the sealing portion of the deformable plane which is sandwiched between the two containers and in contact with the containers (where 0.3 mm<L<10 mm), ν is a Poisson's ratio of the deformable plane, h is thickness of the deformable plane (where 0.2 mm<h<3.0 mm), and t is amount of compression of the deformable plane by the mechanical seal (where 0.05<t/h<0.50), the deformable plane has a flat plate shape by the fact that the liquid chamber and the air chamber have a pressure equal to atmospheric pressure when the deformable plane is mechanically sealed under condition of a tensile displacement λ which satisfies an expression:

$$-\nu \times L \times (t+h)/2 < \lambda;$$

(f) the pressure sensor for an extracorporeal circulating circuit according to (d), wherein the deformable plane has a ring section having a thickness larger than that of the deformable plane at the periphery thereof as a sealed portion; and on the assumption that La is width of the sealing portion of the ring section which is sandwiched between the two containers and in contact with the containers (where 0.3 mm<La<10 mm), νa is a Poisson's ratio of the ring section, and ha is thickness of the ring section (where 1.0 mm<ha<5.0 mm), and ta is amount of compression of the ring section by the mechanical seal (where 0.05<ta/ha<0.50), the deformable plane has a flat plate shape by the fact that the liquid chamber and the air chamber have a pressure equal to atmospheric pressure when the deformable plane is mechanically sealed under condition of a tensile displacement λ which satisfies an expression: $-\nu a \times La \times (ta+ha)/2 < \lambda$;

(g) the pressure sensor according to (f) wherein the ring section has a circular cross section;

(h) the pressure sensor for an extracorporeal circulating circuit according to (f) or (g), wherein the sealing portion of the air chamber and/or the sealing portion of the liquid chamber is provided with a groove into which the ring section is inserted, and the groove has inner surfaces which are inclined relative to the deformable plane to form an acute angle therebetween;

(i) the pressure sensor for an extracorporeal circulating circuit according to any one of (d) to (h), further including: an air chamber adjusting to atmospheric pressure means for pressurizing the air chamber to atmospheric pressure; a liquid chamber adjusting to atmospheric pressure means for pressurizing the liquid chamber to atmospheric pressure; a liquid chamber pressure controlling means for controlling a pressure in the liquid chamber; a liquid chamber pressure measuring means for measuring a pressure in the liquid chamber; and a damage detecting means for detecting damage of the deformable plane by changing a pressure in the liquid chamber to measure a pressure in the air chamber corresponding to the pressure in the liquid chamber for comparison;

(j) the pressure sensor for an extracorporeal circulating circuit according to (i), wherein after the air chamber adjusting to atmospheric pressure means and the liquid chamber adjusting to atmospheric pressure means pressurize the air chamber and the liquid chamber to atmospheric pressure respectively, on the assumption that the pressure in the liquid chamber when the deformable plane closely contacts a wall surface of the air chamber by increasing the pressure in the liquid chamber using the liquid chamber pressure controlling means is P1, the damage detecting means determines that the deformable plane is damaged when the liquid chamber pressure controlling means further increases the pressure in the liquid chamber up to P2 (>P1) and the pressure in the air chamber becomes higher than P1;

(k) the pressure sensor for an extracorporeal circulating circuit according to (i), wherein after the air chamber adjusting to atmospheric pressure means and the liquid chamber adjusting to atmospheric pressure means pressurize the air chamber and the liquid chamber to atmospheric pressure respectively, on the assumption that the pressure in the liquid chamber when the deformable plane closely contacts a wall surface of the liquid chamber by decreasing the pressure in the liquid chamber using the liquid chamber pressure controlling means is P3, the damage detecting means determines that the deformable plane is damaged when the liquid chamber pressure controlling means further decreases the pressure in the liquid chamber up to P4 (<P3) and the pressure in the air chamber becomes lower than P3;

(l) the pressure sensor for an extracorporeal circulating circuit according to (i), wherein the damage detecting means memorizes characteristics of a change of a pressure in the air chamber corresponding to a pressure in the liquid chamber in advance; and after the air chamber adjusting to atmospheric pressure means and the liquid chamber adjusting to atmospheric pressure means pressurize the air chamber and the liquid chamber to atmospheric pressure respectively, the liquid chamber pressure controlling means increases or decreases the pressure in the liquid chamber; and then the damage detecting means determines that the deformable plane is damaged when the change of the pressure in the air chamber corresponding to the change of the pressure in the liquid chamber which is measured by the liquid chamber pressure measuring means is different from the characteristics of the change of the pressure in the air chamber which is memorized in advance;

(m) the pressure sensor for an extracorporeal circulating circuit according to any one of (d) to (l), wherein the air chamber and the liquid chamber are housed in a common casing, and the pressure sensor in the extracorporeal circulating circuit further includes an attachment surface to which the casing is attached, and an attachment sensing means for detecting the attachment of the casing to the attachment surface, wherein the attachment surface is configured to have the communication section with an opening which is connectable to the air inlet/outlet of the air chamber, so that the air inlet/outlet and the communication section are connected to each other in an air tight manner when the attachment sensing means detects attachment of the casing;

(n) the pressure sensor for an extracorporeal circulating circuit according to (m), wherein the attachment sensing means is attached to the casing;

(o) the pressure sensor for an extracorporeal circulating circuit according to (m), wherein the attachment sensing means is attached to the attachment surface;

(p) the pressure sensor for an extracorporeal circulating circuit according to (m) or (o), wherein the attachment surface has a cushioning section around the opening of the communication section for applying a force toward the casing, and the cushioning section is movable toward the connection between the air inlet/outlet and the communication section;

(q) the pressure sensor for an extracorporeal circulating circuit according to any one of (m) to (p), wherein the attachment sensing means detects the contact between the casing and the attachment surface when the casing is attached to the attachment surface;

(r) the pressure sensor for an extracorporeal circulating circuit according to any one of (m) to (p), wherein the attachment sensing means detects that the casing is attached to a predetermined position after rotating along the attachment surface; and (s) the pressure sensor for an extracorporeal circulating circuit according to any one of (m) to (p), further including a rotating body around the casing, wherein the attachment sensing means detects that the rotating body is attached to a predetermined position after rotating along the attachment surface.

BEST MODE FOR CARRYING OUT THE INVENTION

With reference to the drawings, embodiments of a pressure sensor for an extracorporeal circulating circuit according to the present invention will be explained below, but the present invention is not limited to the embodiments. FIG. 1 is a schematic view showing a pressure sensor of the present embodiment.

In FIG. 1, a pressure sensor 1 is disposed on a liquid flow path 8, and is configured with: a liquid chamber 6 having reference plane 10 which is not deformed by a pressure in the liquid flow path, a deformable plane 20 which is disposed separately from the reference plane 10 and is at least partially deformed by a pressure in the liquid flow path, a first connecting plane 11 which is not deformed by a pressure in the liquid flow path and connects the deformable plane 20 with the reference plane 10 to form a closed liquid-tight space therein, a liquid flow inlet 40 which is provided on a side surface of the first connecting plane 11, and a liquid flow outlet 41 which is disposed at a position separated from the liquid flow inlet 40 in the direction of a flow of a liquid which is introduced along an inner circumference of side surfaces of the first connecting plane 11 by a distance from more than one half to less than one of the inner circumference; a pressure measuring means 7 which is disposed outside of for measuring a pressure in the liquid chamber 6 by measuring a deformation quantity of the deformable plane 20, and is a load sensor 45 or a strain gauge 46; and a liquid flow path 8 which is connected to the liquid flow inlet 40 in a liquid tight manner and is disposed so that the liquid introduced in the liquid chamber 6 flows in along the inner circumference of the first connecting plane 11.

In FIG. 2, the pressure sensor 1 further includes: an opposing plane 30 which is not deformed by a pressure and is disposed separately from the deformable plane 20 so that the deformable plane 20 is located in the middle between the reference plane 10 and the opposing plane 30; a second connecting plane 31 which is not deformed by a pressure and connects the opposing plane 30 with the deformable plane 20 to form a closed liquid-tight space therein; and an air chamber 9 having an air inlet/outlet 50 which is provided in a side surface of the second connecting plane 31 or the opposing plane 30. When the pressure in the liquid flow path 8 is changed, the pressure in the air chamber 9 which forms an air-tight space between the deformable plane 20 and the opposing plane 30 is changed. Furthermore, the pressure sensor 1 is configured with: the pressure measuring means 7 which indirectly measures a pressure in the liquid flow path 8 by measuring the change of the pressure using an air chamber pressure measuring means 60 via a communication section 51; and the liquid flow path 8 which is connected to the liquid flow inlet 40 in a liquid tight manner and is disposed so that the liquid introduced in the liquid chamber 6 flows in along the inner circumference of the first connecting plane 11.

(Shape)

In FIG. 1, the reference plane 10 is circular, but as shown in FIG. 3, may be polygonal such as octagonal. Also, it is not problem if the reference plane 10 and the deformable plane 20 have different shapes and sizes from each other as shown in FIG. 4. In FIG. 1, reference plane 10 has a flat plate shape, but if the reference plane 10 has uneven surfaces, in some cases, a liquid can be more effectively exchanges as will be explained later. Thus, there is no limitation on the surface shape of the reference plane 10. However, in order to make a liquid flow more smoothly, as shown in FIG. 1, preferably the reference plane 10 is circular and has a flat plate shape, the deformable plane 20 is circular, and the reference plane 10 and the deformable plane 20 have a shape of the same size.

In FIG. 1, the first connecting plane 11 has a linear cross section, but as shown in FIG. 5, the junction between the reference plane 10 and the first connecting plane 11 and the junction between deformable plane 20 and the first connecting plane 11 may include inclined planes to form an angle of about 45 degrees therebetween, instead of 90 degrees. Also, as shown in FIG. 6, the junction between the reference plane 10 and the first connecting plane 11 and the junction between deformable plane 20 and the first connecting plane 11 may include the junction in the rounded shape. In addition, as shown in FIG. 7, the reference plane 10 and the deformable plane 20 may be round as a whole.

Any configuration of FIG. 2 to FIG. 7 may be used, but preferably the connection between a reference plane and a connecting surface has a certain roundness as shown in FIGS. 6 and 7.

Moreover, in FIG. 1, the deformable plane 20 has a flat plate shape, but as shown in FIG. 8, may have a cross section of a triangle wave shape or a shape such as a sine wave. However, for the reasons which will be explained later, the deformable plane 20 most desirably has a flat plate shape. Also, in FIGS. 1 and 7, the entire deformable plane 20 provides the deforming section as a deformable portion of the deformable plane 20. However, the deformable plane 20 may include the deforming section having an area at any rate of the entire deformable plane 20, and also the deforming section may have any shape, as far as the section can be correctly measured. As far as the section can be correctly measured, there is no limitation on the rate and the shape.

In FIG. 1, the liquid flow path 8 is parallel to the reference plane 10, but as shown in FIG. 9, the liquid flow path 8 may be slightly inclined, which does not deteriorate the effect of the above invention. However, in order to make a liquid flow more smoothly, the liquid flow path 8 preferably forms an angle of from 0 to 30 degrees relative to the reference plane 10, more preferably 0 to 15 degrees, and most preferably the liquid flow path 8 is parallel to the reference plane 10.

In FIG. 1, a tangential plane 12 of the inner surface of the liquid flow path 8 is in contact with the inner surface of the first connecting plane 11, and the liquid flow path 8 connected to the liquid flow inlet 40 is completely disposed along the side surface of the first connecting plane 11, but as shown in FIG. 10, the tangential plane 12 of the inner surface of the liquid flow path 8 may be offset toward the center, which does not deteriorate the effect of the above invention. However, in order to make a liquid flow more smoothly, the tangential plane 12 of the inner surface of the liquid flow path 8 is desirably disposed at a position spaced 0 to 3 mm or less inwardly in the normal direction from the inner surface of the first connecting plane 11, more preferably 0 to 2 mm or less, and most preferably 0 to 1 mm.

The liquid flow outlet 41 is disposed at the highest position of the circular shape in FIG. 1, but may be placed at the other position as shown in FIG. 11. In this case, when the pressure sensor 1 is disposed so that the liquid flow inlet 40 is parallel to gravity, in flowing a liquid, the air remains in the upper space 65 in the liquid chamber 6, and the body fluid or medicinal solution contacts the air in the pressure sensor 1, which may cause coagulation of the body fluid or medicinal solution. However, since a turning of the pressure sensor 1 to change its orientation during treatment can cause the air in the pressure sensor 1 to be discharged, the effects of the above invention are not deteriorated. Therefore, there is no limitation on the position of the liquid flow outlet 41.

In FIG. 1, the liquid flow outlet 41 is disposed at a position spaced from the liquid flow inlet 40 in the direction of a flow of a liquid wherein the liquid is introduced in the liquid chamber 6 along the inner circumference of side surfaces of the first connecting plane 11 from the liquid flow inlet 40 by a distance of ¾ of the inner circumference, and the liquid flow outlet 41 is connected to the liquid chamber 6 so that the direction to which the liquid flows out is at an angle of 180 degrees to the direction to which the liquid flows in. However, as shown in FIG. 12, the liquid flow outlet 41 may be disposed at a position spaced from the liquid flow inlet 40 in the direction to which a liquid is introduced in the liquid chamber 6 along the inner circumference of the first connecting plane 11 from the liquid flow inlet 40 by a distance of one half of the inner circumference, and may be connected to the liquid flow outlet 41 so that the direction to which the liquid flows out is at an angle of 90 degrees to the direction to which the liquid flows in, which does not deteriorate the effect of the above invention.

It is particularly preferable that the liquid flow outlet 41 is disposed at a position spaced from the liquid flow inlet 40 in the direction to which a liquid is introduced in the liquid chamber 6 along the inner circumference of the first connecting plane 11 from the liquid flow inlet 40 by a distance of from more than one half of the inner circumference to less than one of the inner circumference. The angle at which the liquid flows in relative to the direction the liquid flows out may be appropriately set depending on the condition for use because the angle does not particularly change the flow in the liquid chamber 6, and therefore, there is no limitation on the direction.

In addition, in FIG. 1, the liquid flow inlet 40 and the liquid flow outlet 41 are disposed centrally between the reference plane 10 and the deformable plane 20, wherein viewed from the cross sectional direction of the liquid flow inlet 40 and the liquid flow outlet 41. However, as shown when viewed from FIG. 13, the liquid flow inlet 40 and the liquid flow outlet 41 may be offset toward the reference plane 10 side or the deformable plane 20 side, which does not deteriorate the effect of the above invention, and there is no limitation on the disposition. However, in order to make a more smooth liquid flow, the liquid flow inlet 40 is preferably disposed at a position spaced 0 to 3 mm from the central point between the reference plane 10 and the deformable plane 20, more preferably 0 to 2 mm, and most preferably 0 to 1 mm. The direction to which the liquid flows out of liquid flow outlet 41 does not particularly affect the flow in the liquid chamber 6 and does not deteriorate the effect of the above invention. Therefore, there is no limitation on the direction.

In FIG. 1, the liquid flow inlet 40 and the liquid flow outlet 41 are disposed on the same plane which is parallel to the reference plane 10. However, even if the liquid flow inlet 40 and the liquid flow outlet 41 may not be disposed on the same parallel plane as shown in FIG. 13, which does not deteriorate the effect of the above invention, and there is no limitation on the disposition. That is, the liquid flow inlet 40 and the liquid flow outlet 41 may be disposed at positions spaced from the reference plane 10 by difference distances.

In FIG. 2, the air inlet/outlet 50 is disposed at the farthest position from the deformable plane 20 in the air chamber. However, if the air inlet/outlet 50 is disposed at any position, this does not affect the measurements of pressure. Therefore, there is no limitation on the disposition.

(Material)

The liquid chamber 6 and the air chamber 9 may be formed of any soft or hard materials. However, if the shapes of the liquid chamber 6 and the air chamber 9 are changed due to environmental factors such as liquid temperature, air temperature, external force which may deform the liquid chamber 6 and the air chamber 9, it is difficult to correctly perform a measurement of pressure in the liquid flow path 8. Thus, the liquid chamber 6 and the air chamber 9 are preferably formed of a hard material. Moreover, since the liquid chamber 6 and the air chamber 9 contact directly or indirectly the body fluid of a patient, the material having biocompatibility is preferable. The material may be polyvinyl chloride, polycarbonate, polypropylene, polyethylene, polyurethane, or the like for example, and any of these can be preferably used. The liquid chamber 6 and the air chamber 9 may be manufactured by any method without any limitation, and the method includes injection molding, blow molding, and cutting.

If the deforming section of the deformable plane 20 which is at least partially deformed by a pressure is formed of a hard material, only a small deformation quantity is obtained when a pressure is applied, which makes it difficult to correctly measure the pressure in the liquid flow path 8. Therefore, the deforming section is preferably formed of a soft material which is flexibly deformed by a pressure. Moreover, since the deforming section directly or indirectly contacts the body fluid of a patient, the material having biocompatibility is preferable. The material may be polyvinyl chloride, silicon resin, styrene thermoplastic elastomer, styrene thermoplastic elastomer compound, or the like for example, and any of these can be preferably used. The remained section (which does not deform) may be of any material, as far as it is formed of the same material as that of the liquid chamber 6 and the air chamber 9.

The liquid flow path 8 may be formed of any one of synthetic resin, metal, glass, and the like. From the viewpoint of manufacturing cost, processability, and operability, a synthetic resin, in particular a thermoplastic resin is preferable as a material of the liquid flow path 8. The thermoplastic resin includes polyolefin resin, polyamide resin, polyester resin, polyurethane resin, fluoro resin, silicon resin, and the like, and also includes ABS (acrylonitrile-butadiene-styrene copolymer) resin, polyvinyl chloride, polycarbonate, polystyrene, polyacrylate, polyacetal, and the like, and any of these can be preferably used. Among these, a soft material is preferable because it is resistant against bending and cracking, and has flexibility in operation. For the reason of assembility, soft polyvinyl chloride is particularly preferable. The communication section 51 may be formed of any material as far as it makes a communication with air chamber 30 to the air chamber pressure measuring means 60, and the material may be any one of synthetic resin, metal, glass, and the like. From the viewpoint of manufacturing cost, processability, and operability, a synthetic resin, in particular a thermoplastic resin is preferable. The thermoplastic resin includes polyolefin resin, polyamide resin, polyester resin, polyurethane resin, fluoro resin, silicon resin, and the like, and also includes ABS (acrylonitrile-butadiene-styrene copolymer) resin, polyvinyl chloride, polycarbonate, polystyrene, polyacrylate, polyacetal, and the like, and any of these can be preferably used. Among these, a soft material is preferable because it is resistant against bending and cracking, and has flexibility in operation. For the reason of assembly, soft polyvinyl chloride is particularly preferable.

(Bonding Method)

The individual bonding method of the liquid chamber 6, the air chamber 9, the liquid flow path 8 generally includes, but are not limited to, hot melt bonding and adhesion for a bonding of a synthetic resin. For example, the hot melt bonding includes high frequency welding, induction welding, ultrasonic welding, friction welding, spin welding, heat plate welding, hot wire welding, and the like. The adhesive type includes cyanoacrylate, epoxy, polyurethane, synthetic rubber, ultraviolet curing type, modified acrylic resin, hot melt type, and the like.

There is no limitation on the bonding method for bonding the deforming section and the remaining section of the deformable plane 20. Generally, a bonding method between a hard material and a soft material includes a mechanical seal in which a hard material holds a soft material therein for sealing, and other methods such as hot melt bonding and adhesion as described above.

The pressure sensor 1 may be used as it is after molding and bonding, but particularly in medical applications in extracorporeal circulation therapy, the pressure sensor 1 is used after sterilization. The sterilization method can be consistent of those of ordinary medical tools, and may use medicinal solution, gas, radiation, high-pressure steam, heat, and the like.

(Size)

When the pressure sensor 1 has a very large size of the reference plane 10, the deformable plane 20, and the first connecting plane 11, the volume of the liquid chamber 6 is increased, which increases a priming volume. To the contrary, when the pressure sensor 1 has a very small size of these components, a negative pressure is produced in the extracorporeal circulating circuit, and the deformable plane 20 is expanded toward the reference plane 10 side, which causes the deformable plane 20 to block the liquid flow inlet 40 and the liquid flow outlet 41, resulting in a problem that the liquid therein does not flow. Therefore, the reference plane 10 preferably has a diameter within a range of about 15 mm to 40 mm, more preferably about 20 mm to 30 mm, and the connecting plane 11 preferably has a height of 5 mm to 20 mm, and more preferably 5 mm to 10 mm. The shape will be described later in the section of design approach.

The liquid flow path 8 may have an inner diameter of any size which is selected in accordance with each extracorporeal circulation therapy, and therefore, there is no limitation on the size. For example, in blood purification therapy which is one extracorporeal circulation therapy, a main tube having an inner diameter of about 2 mm to 5 mm is generally selected. The liquid flow path 8 does not need to have a circular cross section, and may have non-circular cross section such as elliptical cross section, rectangular cross section, and hexagonal cross section.

(Liquid)

The liquid which flows through the pressure sensor 1 may be any body fluid or medicinal solution. Therefore, there is no limitation on the liquid. The body fluid may be for example blood, plasma, lymph, tissue fluid, mucus, hormone, cytokine, urine, or the like. The medicinal solution may be for example isotonic sodium chloride solution, anticoagulant, fresh frozen plasma, dialysis solution, albumin solution, filter-type replacement fluid for artificial kidney, or the like.

Next, another embodiment of a pressure sensor according to the present invention will be explained below using figures. FIG. 14 is a schematic view showing a pressure sensor 1. The parts which have the same functions as those of the above described embodiment are designated by the same reference numerals, which will not be explained below. The pressure sensor 1 of the present embodiment is similar to the pressure sensor 1 of the above described embodiment except a baffle plate 66 is disposed near the connecting plane between the liquid flow inlet 40 and the liquid flow outlet 41. The baffle plate 66 disturbs the flow of a fluid. The baffle plate 66 is arranged so that the fluid introduced in the liquid chamber 6 flows in substantially in parallel to the reference plane 10 along the inner circumference of side surfaces of the first connecting plane 11, so that a circulating flow in the liquid chamber 6 is formed to prevent any retention of the body fluid or medicinal solution.

In the present embodiment, the baffle plate 66 which is disposed near the connecting plane between the liquid flow inlet 40 and the liquid flow outlet 41 to disturbs the flow of a fluid, which enables an enhancement of the more effective exchange of the liquid in the casing. In short, in addition to a circulating flow in the liquid chamber 6, a flow toward the center of the liquid chamber 6 are formed, as the result of that the turbulence in the liquid chamber 6 is increased, and the replacement of the body fluid or medicinal solution in the liquid chamber 6 can be accelerated.

The baffle plate 66 may be disposed at any position, but is preferably disposed at a position which is in contact with the first connecting plane 11 and has the highest rate of a liquid flow. In FIG. 14, the baffle plate 66 is disposed at a position adjacent to the liquid flow outlet 41 in the longer distance between the liquid flow inlet 40 and the liquid flow outlet 41. However, as shown in FIG. 15, baffle plate 66 may be disposed on the first connecting plane 11 opposite to the liquid flow outlet 41, which does not deteriorate the effect of the above invention, and there is no limitation on the disposed position.

The baffle plate 66 of a very large size is interfered with the deformable plane 20 after deformation, and the baffle plate 66 of a very small size can not exert it's effect. Therefore, the baffle plate 66 preferably has a width in the diameter direction within a range of about 5% to 15% of the diameter of the reference plane 10, more preferably about 10% to 15%, and also preferably has a height within a range of about 30% to 80% of the height of the side of the first connecting plane 11, more preferably about 50% to 70%, but there is no particular limitation on these values.

The baffle plate 66 may have a polygonal shape such as triangular shape as shown in FIG. 14 or a polygonal shape with round corners when viewed from the reference plane 10. The baffle plate 66 may have any shape as far as the baffle plate 66 can exert its effect without particular limitation. In FIG. 14, only one baffle plate 66 is disposed, but when two or more baffle plates 66 are disposed, the effects of the above invention can be enhanced. The number of the disposed baffle plates 66 and the space between the baffle plates 66 may be appropriately set depending on the flow rate in use, and there is no particular limitation on these values. However, the facts that a plurality of the baffle plates 66 are set up are meaningless if the baffle plates 66 become a very small space therebetween. Also, since a retention in the flow may be generated downstream of the baffle plates 66, it is not preferable to dispose a very large number of the baffle plates 66. Thus, when a plurality of the baffle plates 66 are disposed, the number of the disposed baffle plates 66 is desirably about 4 at most. The baffle plates 66 are spaced from each other by a distance of 15% to 25% or more of the peripheral length of the first connecting plane 11, more preferably 20% to 25% or more.

[Design Approach]

With reference to FIG. 2, the most appropriate design approach of the container when the pressure measuring means 7 is the air chamber pressure measuring means 60 will be explained below.

As shown in FIG. 2, the pressure sensor 1 is configured with the air chamber 9 having the air inlet/outlet 50, the liquid chamber 6 having the liquid flow inlet 40 and the liquid flow outlet 41, the deformable plane 20 which is sandwiched between the air chamber 9 and the liquid chamber 6 to separate the air chamber 9 and the liquid chamber 6 and is deformed depending on the differences between the pressure in the air chamber and the pressure in the liquid chamber, and the air chamber pressure measuring means 60 which is connected to the air inlet/outlet 50 of the air chamber 9 via the communication section 51 and measures the pressure in the liquid chamber through the deformable plane 20 on the air chamber side.

In the air chamber 9, the deformable plane 20 is deformed toward the air chamber side by a positive pressure in the liquid chamber. Thus, the air chamber 9 should have a volume which is equal to the deformation quantity of the deformable plane 20 at the possible maximum pressure.

On the assumption that $V_A$ is volume of the air chamber 9 in the initial state, $P_A$ is pressure in the air chamber 9 in the initial state, $V_T$ is volume of the communication section 51, $P_{MAX}$ is the maximum measurable pressure of the pressure sensor, and $P_0$ is atmospheric pressure, and further the following Expression (1a) is satisfied, a pressure can be measured even under the maximum pressure. Herein, the initial state means the point of time when a pressure measurement starts, and $P_A$ and $P_{MAX}$ are expressed as gage pressure, and $P_0$ is expressed as absolute pressure. The gage pressure means a pressure which is measured under atmospheric pressure condition, while the absolute pressure means a pressure which is measured based under vacuum condition.

$$(P_A+P_0) \times (V_A+V_T) > (P_{MAX}+P_0) \times V_T \quad (1a)$$

The following expression can be obtained from Expression (1a):

$$\{(P_{MAX}+P_0) \div (P_A+P_0) - 1\} \times V_T < V_A \quad (1)$$

which determines the volume of the air chamber 9.

Next, in the liquid chamber 6, the deformable plane 20 is deformed toward the liquid chamber side when the liquid chamber has a negative pressure therein. Thus, the liquid chamber 6 should have a volume equal to the volume the deformable plane may be deformed at a possible minimum pressure.

On the assumption that $V_L$ is volume in the initial state of the liquid chamber 6 and $P_{MIN}$ is the minimum measurable pressure of the pressure sensor, and further the following Expression (2a) is satisfied, a pressure can be measured even under the minimum pressure.

$$(P_{MIN}+P_0) \times (V_A+V_T+V_L) > (P_A+P_0) \times (V_A+V_T) \quad (2a)$$

The following expression can be obtained from Expression (2a):

$$V_L > \{(P_A+P_0) \div (P_{MIN}+P_0) - 1\} \times (V_A+V_T) \quad (2b)$$

which determines the volume of the liquid chamber 6. $P_{MIN}$ is expressed as gage pressure.

However, the liquid chamber 6 having a large volume is advantageous in measuring a negative pressure, but increases a priming volume. Thus, the liquid chamber preferably has a volume of 1 ml to 10 ml, and more preferably 2 ml to 5 ml. As a result, the air chamber 9 preferably has a volume of 0.2 ml to 1.0 ml, and more preferably 0.3 ml to 0.8 ml. Thus, Expression (2b) should further satisfy the following Expression (2):

$$\{(P_A+P_0) \div (P_{MIN}+P_0) - 1\} \times (V_A+V_T) < V_L < 10 \text{ mL} \quad (2)$$

where the volume of the air chamber 9 does not include the air inlet/outlet 50. The volume of the communication section 51 includes the volume of the air inlet/outlet 50 and the inner volume of the air chamber pressure measuring means 60. The volume of the liquid chamber 20 does not include the volume of the liquid flow inlet 40 and the volume of the liquid flow outlet 41.

Generally, in blood purification therapy (extracorporeal circulation therapy), the pressure $P_A$ of the air chamber 9 in the initial state is often equal to the atmospheric pressure $P_0$. However, it is also possible to create an advantageous condition for measuring a positive pressure by applying a pressure in advance to the positive pressure side. And vice versa, it is also possible to create an advantageous condition for measuring a negative pressure by producing a negative pressure $P_A$ on the air chamber side in the initial state.

The pressures $P_{MIN}$ and $P_{MAX}$ can be measured with no difficulties within the range which is usually used in blood purification. Thus, the pressures $P_{MIN}$, $P_{MAX}$, and $P_A$ within the following range can be measured with no difficulties:

−600 mmHg<$P_{MIN}$<−200 mmHg 200 mmHg<$P_{MAX}$<600 mmHg

−200 mmHg<$P_A$<200 mmHg

The communication section 51 having a very large volume $V_T$ increases the volumes of the air chamber 9 and the liquid chamber 6 according to the Expressions (1) and (2), which in turn increases a priming volume. To the contrary, the communication section 51 having a very small volume $V_T$ decreases the distance from the air inlet/outlet 50 to the air chamber pressure measuring means 60, which sacrifices its handling property. Thus, the communication section 51 preferably has a volume of 1 ml or less, more preferably 0.5 ml or less, and most preferably 0.2 ml or less. Ideally, the communication section 51 has a volume of 0 ml including the air inlet/outlet 50, but this is impossible because the air chamber pressure measuring means 60 has a small inner volume. Therefore, there is nothing that Expression (1) is not justified.

The sealing portions 100 and 101 of the deformable plane 20, which are sandwiched between the two containers may have different lengths each other. However, for the reasons of molding and assembly, the positions of the sealing portions 100 and 101 are preferably symmetrical around the central point of the deformable plane.

The deformable plane 20 is a flat plate while the air chamber 9 and the liquid chamber 6 have a pressure equal to the atmospheric pressure $P_0$, and also separates the air chamber 9 and the liquid chamber 6. The deformable plane 20 may use any means for separating the air chamber 9 and the liquid chamber 6 and keeping the containers air-tight, and there is no limitations on the means. The means may be hot melt bonding, adhesion, or mechanical seal as described above. The mechanical seal means that a material such as rubber is sandwiched between the containers to obtain air-tight closure.

When hot melt bonding, adhesion, or mechanical seal is used, in order to contact the air chamber 9 and the liquid chamber 6 with the deformable plane 20 in a more effective manner, the deformable plane 20 is sandwiched and compacted (mechanically sealed) to various degrees. However, as shown in FIG. 16, only a mechanical seal in the direction shown by the arrow 110 produces a deformation of the deformable plane from the flat plate, resulting in a change of the volumes of the liquid chamber and the air chamber. In this case, it is difficult to make the deformable plane 20 keep to have a flat plate shape when the liquid chamber and the air chamber has a pressure equal to the atmospheric pressure $P_0$.

Then as shown in FIG. 17, the above problem can be solved by compressing in the direction of the arrow 110 and by mechanically sealing the container on the air chamber side and the container on the liquid chamber side, while the deformable plane 20 is pulled in direction of the arrow 111.

That is, on the assumption that h is thickness of the deformable plane 20, t is amount of compression, ν is Poisson's ratio (the difference between a longitudinal strain and a transversal strain of an object caused by tension or compression), and L is total length of the sealing portions 100 and 101 when the deformable plane 20 is sandwiched between two containers and the containers and the deformable plane 20 are in contact with each other, it is known that the deformable plane 20 is expanded in the direction perpendicular to the direction of the compression by the volume expressed by Expression (3a) when being compressed in the direction of the arrow 110:

$$-\nu \times L \times (t+h) \quad (3a)$$

On the assumption that the deformable plane 20 symmetrically expands on right and left sides, one half of the expanded volume by the Expression (3a) is produced in the direction toward the central point of the deformable plane 20. Thus, when the mechanical seal is performed with at least one half of the volume by the Expression (3a) being tensed to the direction shown by the arrow 111 of FIG. 17, the sealing can be achieved without any change in the initial position of the deformable plane 20 even if the deformable plane 20 is expanded in direction toward the central point of the deformable plane 20. Therefore, the tensile displacement λ which satisfies Expression (3) can be used:

$$-\nu \times L \times (t+h)/2 < \lambda \quad (3)$$

In FIG. 17, the deformable plane 20 and the portion sandwiched between the two containers (sealing portions 100 and 101) are configured to be parallel to each other. However, as shown in FIG. 18, the sealing portions 100 and 101 may be inclined relative to the deformable plane 20 by a certain angle, and as shown in FIG. 19, at least one surface of the portion sandwiched between the two containers may have a convexo-concave structure 120 which has a rectangular shape, triangular shape, wavy shape, or the like. From the viewpoint of manufacturing cost, and assembly, preferably the deformable plane 20 and the portion sandwiched between the two containers are parallel to each other, and have flat surfaces.

The deformable plane 20 having a flat plate shape does not change the volume of the air chamber 9 when a tensile stress which satisfying Expression (3) is applied to the deformable plane 20. In addition, the deformable plane 20 does not affect a pressure measuring at all, because when a tensile stress is applied, there is generally a proportional relationship between load and elongation before a yield point. The yield point herein means the point where a deformation is generated without any increase of applied power, and beyond the point, the deformed material does not recover its original shape.

The tensile stress can be strictly applied up to the value which is obtained by subtracting the deformation quantity of the deformable plane from the value at the yield point. However, an excess tensile stress makes the manufacturing of the pressure sensor difficult. Thus, the volume of the tensile stress applied to the deformable plane is preferably one to five times (inclusive) of the minimum value of Expression (3), and more preferably one to three times (inclusive) of the minimum value of Expression (3).

The deformable plane having a flat plate shape does not cause a problem of fluid retention on the surfaces of the deformable plane or frictional secondary flow, which solves the problem of the coagulation of body fluid or medicinal solution. In FIG. 2, the air chamber 9 has a rectangular cross section, but may have a cross section of a dome shape or polygonal shape. Preferably, the air chamber 9 has a cross section of a dome shape which follows the deformation of the deformable plane most easily.

The deformable plane 20 is sandwiched between the container on the air chamber side and the container on the liquid chamber side at its peripheral portion to be mechanically sealed. The sealing portion and the diaphragm may be circular, elliptical, rectangular, polygonal, or the like. For the reasons of molding and assembly, the sealing portion and the diaphragm are particularly preferably circular.

At the inside of the sealing portion of the deformable plane 20, the unsealing portion having a smaller diameter has to compensate a pressure difference to a larger degree. That is, in the case of an unsealing portion having a smaller diameter, the deformation quantity of the deformable plane 20 is larger than the case with a larger diameter, in order to change the volume to the same degree as in the case with the larger diameter. As the deformation quantity of the deformable plane 20 is increased, the force required to change the deformable plane 20 is increased. Therefore, the proportional relationship between the force and the deformation quantity of the deformable plane 20 is distorted, and the difference between the pressure in the liquid chamber and the pressure in the air chamber increases, thereby resulting in that a large amount of compensation is required.

At the inside of the sealing portion of the deformable plane 20, when the unsealing portion has a larger diameter, the difference between the inner diameter of the liquid flow inlet and the inner diameter of the deformable plane is increased, and retention of the body fluid or medicinal solution in the liquid chamber is easily generated. Thus, the unsealing portion preferably has a larger diameter of 10 mm to 50 mm, and more preferably of 20 mm to 30 mm.

The unsealing portion of the deformable plane 20 having a very small thickness is easily damaged and causes leakage, while the unsealing portion having a very large thickness is hardly deformed by the change in pressures in the liquid chamber. Thus, the unsealing portion preferably has a thickness of 0.2 mm to 3.0 mm, and more preferably of 0.3 mm to 0.7 mm.

The amount of compression (t) is generally, for mechanical seal, at a ratio (t/h) to a thickness (h) of the deformable plane of 50% or less, more preferably of about 5% to 50%, but the amount of compression may be appropriately determined to be at any ratio as far as leakage is not caused.

The sealing portions 100 and 101 having a very small width L cannot exert the seal effects, and the sealing portions 100 and 101 having a very large width L makes the size of the sensor large. Thus, the sealing portions 100 and 101 preferably have a width L of 0.3 mm to 10 mm, and more preferably of 0.3 mm to 5 mm. When the sealing portions 100 and 101 have a shape like a ring section which will be explained in a third embodiment, a reduction of a width L of the sealing portions 100 and 101 is possible, which is useful to make the size of the apparatus small.

Next, another embodiment of a pressure sensor according to the present invention will be explained below with reference to figures. FIG. 20 is a schematic view showing a deformable plane of a pressure sensor of the present embodiment: FIG. 20(a) is a side view of the deformable plane; and FIG. 20(b) is a plane view of the deformable plane. The same parts as those in the first embodiment are designated by the same reference numerals as those in the first embodiment, but the explanation thereof will be omitted below.

In the above embodiment, the deformable plane 20 having a flat plate shape is sealed: when the deformable plane 20 has a thickness of 0.5 mm for example, and 20% of the thickness is compressed, the thickness of 0.1 mm is compressed. However, such a compression of 0.1 mm to the deformable plane 20 having a thickness of 0.5 mm inevitably requires a high precision in manufacturing and increases the cost.

In the present embodiment, the deformable plane 20 (the gray colored portion in FIG. 20) has a ring section 130 along the periphery thereof. The ring section 130 has a larger thickness than that of the deformable plane 20. This expands the allowable error range of the manufacturing precision in mechanical seal. That is, assuming that the ring section 130 has a thickness of 2 mm and the 20% of the thickness is compressed, the thickness of 0.4 mm is compressed. This definitely secures a compression of 15% even if only thickness of 0.3 mm is compressed due to manufacturing error, which allows the compressed portion to have the property of a typical seal.

The ring section 130 may have any thickness. However, the ring section 130 having a very large thickness increases the size of the sensor, and the ring section 130 having a very small thickness narrows the allowable error range. Thus, the ring section 130 preferably has a thickness of 1 mm to 5 mm, and more preferably of 1 mm to 3 mm.

In FIG. 20, the ring section 130 has a rectangular cross section. Generally known sealing materials have a cross section of a shape such as circle, ellipse, triangle, and X-ring for example, and any of these can be preferably used. From the viewpoint of manufacturing cost and assembly, most preferably the ring section 130 has a circular cross section. In FIG. 20, the deformable plane 20 is coupled to the ring section 130 at the center of the cross section of the ring section 130. However, the deformable plane 20 may be jointed at an upper/lower end of the cross section of the ring section 130, and there is no particular limitation on the position of the joint.

When deformable plane 20 has the ring section 130, and the container on the air chamber side and the container on the liquid chamber side has a certain device, a tensile displacement λ can be easily applied to the deformable plane 20. For example, as shown in FIG. 21, the sealing portions 100 and 101 of the air chamber 9 and/or the liquid chamber 6 are provided with a groove to which the ring section 130 is inserted. The groove has a depth, and the deformable plane 20 and the ring section 130 has a height, and there is an offset therebetween, which allows a tensile displacement λ to be automatically applied in a mechanical seal. The groove to which the ring section 130 in FIG. 21 is inserted has inner surfaces which are inclined to form an acute angle relative to the deformable plane 20, so that the ring section is spread along the surfaces in a mechanical seal. There are various examples other than the above configuration, and there is no particular limitation on the means.

(Detection of Damage of Deformable Plane)

FIG. 22 is a schematic view showing another pressure sensor according to the present embodiment.

As shown in FIG. 22, the pressure sensor 1 is configured with: the casing 4 disposed on the way to the liquid flow path 8, which includes the air chamber 9 with the air inlet/outlet 50, the liquid chamber 6 having the liquid flow inlet 40 and the liquid flow outlet 41, and the deformable plane 20 that is sandwiched between the air chamber 9 and the liquid chamber 6 to separate the air chamber 9 and the liquid chamber 6, and is deformed depending on a pressure difference between the inside of the air chamber 9 and the inside of the liquid chamber 6; the air chamber pressure measuring means 60 which is connected to the air inlet/outlet 50 via the communication section 51 and measures a pressure in the liquid chamber 6 on the air chamber 9 side through the deformable plane 20; the branched line 52 which is branched from the communication section 51; the air chamber adjusting to atmospheric pressure means 81 which is displaced on the branched line 52 for pressurizing the air chamber 9, the communication section 51, and the branched line 52 to atmospheric pressure; liquid chamber pressure measuring means 61 for measuring a pressure in the liquid chamber 6 disposed on the way to the liquid flow path 8; liquid chamber pressure controlling means 70 for increasing or decreasing the pressure in the liquid chamber 6 for control; the liquid chamber adjusting to atmospheric pressure means 80 for pressurizing the liquid chamber 6 to atmospheric pressure; and the damage detecting means 5 for detecting damage of the deformable plane by changing a pressure in the liquid chamber to measure a pressure in the air chamber corresponding to the pressure in the liquid chamber for comparison using the air chamber pressure measuring means 60 and the liquid chamber pressure measuring means 61.

The casing 4 is disposed on the way to the liquid flow path 8 and measures a pressure in the liquid flow path 8. The casing 4 measures a pressure in the liquid chamber 6 by measuring a pressure in the air chamber 9 and converting the value, because a change in the pressure in the liquid chamber 6 causes the deformable plane 20 to be deformed, and then the pressure in the air chamber 9 changes in correlation with the pressure in the liquid chamber.

In the above configuration, when the air chamber adjusting to atmospheric pressure means 81 and the liquid chamber adjusting to atmospheric pressure means 80 are closed, and the pressure in the liquid flow path 8 is gradually increased by the liquid chamber pressure controlling means 70, at a certain value of the pressure, the deformable plane 20 contacts the wall surface of the air chamber 9 and stops deformation. That is, no more measuring of a pressure can be done. On the assumption that P1 is the pressure at this point, when the pressure P1 is further increased to reach a pressure P2 which is larger than P1, the liquid chamber pressure measuring means 61 indicates a measurement of the pressure P2. However, the air chamber pressure measuring means 60 indicates a measurement of the pressure P1. In the meantime, if the deformable plane 20 in the casing 4 is damaged, the air chamber pressure measuring means 60 is in communication with the liquid flow path 8 and the air chamber pressure measuring means 60 indicates a measurement of the pressure P2 when the pressure P1 is further increased to reach a pressure P2. Therefore, the facts that the deformable plane is damaged can be determined.

In other words, the damage detecting means 5 determines that the deformable plane 20 is damaged when the pressure in the air chamber 9 is larger than the pressure P1 in the case where after the pressures in the air chamber 9 and the liquid chamber 6 are pressurized to atmospheric pressure by the air chamber adjusting to atmospheric pressure means 81 and the liquid chamber adjusting to atmospheric pressure means 80, the pressure in the liquid chamber 6 is increased by the liquid chamber pressure controlling means 70 until the deformable plane 20 contacts the wall surface of the air chamber 9, the pressure in the liquid chamber 6 at this point is set to be the pressure P1, and the pressure P1 in the liquid chamber 6 is further increased by the liquid chamber pressure controlling means 70 to a pressure P2 (>P1).

And vice versa, when the air chamber adjusting to atmospheric pressure means 81 and the liquid chamber adjusting to atmospheric pressure means 80 are closed, and the pressure in the liquid flow path 8 is gradually decreased by the liquid chamber pressure controlling means 70, at a certain value of the pressure, the deformable plane 20 contacts the wall surface of the liquid chamber 6 and stops deformation. That is, no more measuring of a pressure can be done. On the assumption that P3 is the pressure at this point, when the pressure P3 is further decreased to reach a pressure P4 which is lower than P3, the liquid chamber pressure measuring means 61 indicates a measurement of the pressure P4. However, the air chamber pressure measuring means 60 indicates a measurement of the pressure P3. In the meantime, if the deformable plane 20 in the casing 4 is damaged, the air chamber pressure measuring means 60 is in communication with the liquid flow path 8, and thus the air chamber pressure measuring means 60 indicates a measurement of the pressure P4 when the pressure P3 is further decreased to reach a pressure P4. Therefore, the facts that the deformable plane is damaged can be determined.

In other words, the damage detecting means 5 determines that the deformable plane 20 is damaged when the pressure in the air chamber 9 is lower than the pressure P3 in the case where after the pressures in the air chamber 9 and the liquid chamber 6 are pressurized to atmospheric pressure by the air chamber adjusting to atmospheric pressure means 81 and the liquid chamber adjusting to atmospheric pressure means 80, the pressure in the liquid chamber 6 is decreased by the liquid chamber pressure controlling means 70 until the deformable plane 20 contacts the wall surface of the liquid chamber 6, the pressure in the liquid chamber 6 at this point is set to be the pressure P3, and the pressure P3 in the liquid chamber 6 is further decreased by the liquid chamber pressure controlling means 70 to a pressure P4 (<P3).

In this case, when the liquid chamber pressure controlling means 70 starts to increase or decrease the pressure, if the volume in the liquid chamber 6 and the air chamber 9 is not stable, i.e. the pressure in the initial state is not stable, the pressures P1 and P3 vary every time they are measured. Therefore, this makes it impossible to measure the pressures correctly. Therefore, at the first stage where damage of the deformable plane is detected, the initial pressures in the liquid chamber 6 and the air chamber 9 should be set to be the same every time detection is conducted. In setting the initial pressures, in order to set the pressures to be atmospheric pressure in the easiest way, the air chamber adjusting to atmospheric pressure means 81 and the liquid chamber adjusting to atmospheric pressure means 80 are opened before the liquid chamber pressure controlling means 70 starts to increase or decrease the pressure, and thereby setting the pressures in the liquid chamber 6 and the air chamber 9 to be atmospheric pressure.

Therefore, any damage of the deformable plane 20 can be detected by the following procedures:

1. Opening the liquid chamber adjusting to atmospheric pressure means 80 and the air chamber adjusting to atmospheric pressure means 81 to pressurize each of the pressure in the liquid chamber 6 and the pressure in the air chamber 9 to atmospheric pressure;
2. Closing liquid chamber adjusting to atmospheric pressure means 80 and the air chamber adjusting to atmospheric pressure means 81;
3. Increasing the pressure in the liquid flow path 8 to the pressure P2 or decreasing to the pressure P4 by the liquid chamber pressure controlling means 70; and
4. Checking that the pressure of air chamber pressure measuring means 60 is not P1 or more or P3 or less.

The pressures P1 and P3 vary depending on the shapes and materials of the air chamber 9, the liquid chamber 6, and the deformable plane 20, but can be measured using the above described method.

There is not any particular limitation on the values of the pressures P2 and P4 to determine a damage of the deformable plane 20, but very large or small values of the pressures P2 and P4 increase the load of the liquid flow path 8. Thus, the pressure P2 is preferably within a range of from P1+10 mmHg to P1+300 mmHg, more preferably from P1+10 mmHg to P1+200 mmHg, and most preferably from P1+10 mmHg to P1+100 mmHg. And the pressure P4 is preferably within a range of from P3−10 mmHg to P3−300 mmHg, more preferably from P3−10 mmHg to P3−200 mmHg, and most preferably from P3−10 mmHg to P3−100 mmHg.

The liquid chamber pressure controlling means 70 may be any pump which is able to supply gas. However, a tube pump to supply the liquid by squeezing tube is preferred which has a function to stop a liquid flow when the pump is stopped. A rotary tube pump is provided with an elastic tube as a liquid supply path, and a rotating body having a plurality of rollers on the outer peripheral portion thereof, and is configured so that a rotation of the rotating body causes the plurality of rollers to squeeze the tube for a supply of liquid. The tube defines an arc having a center that is also the center of the rotating body, so that the plurality of rollers revolves around the center while turning round on their own axes to squeeze the tube for a supply of liquid.

The liquid chamber adjusting to atmospheric pressure means 80 and the air chamber adjusting to atmospheric pressure means 81 may be, for example, forceps, manually-operated clamps, motor-operated valves or the like. The motor-operated valve includes rotary solenoid type, push-pull type, and the like, but any valve may be used as far as the valve can close and open the liquid flow path 8 or a branched line 52 of the communication section 51, and there is no particular limitation on it. Furthermore, the air chamber adjusting to atmospheric pressure means 81 may have a configuration as shown in FIG. 23, instead of that having the branched line 52 of the communication section 51 and the air chamber adjusting to atmospheric pressure means 81. That is, a configuration may be used in which the casing 4 is removable from the communication section 51, and connecting means 55 of the communication section 51 is used to attach and remove the casing 4 to and from the communication section 51 so that the air chamber 9 can be closed and also pressurized to atmosphere pressure.

The connecting means 55 of the communication section 51 may be a luer connector, a coupler, a sleeve-shaped tube for insertion, or the like. The connecting means 55 may be any means which can connect between the casing 4 and the communication section 51 in air-tight manner, and there is no particular limitation on it. In FIG. 23, the communication section 51 is included in the casing 4. However, the connecting means 55 of the communication section 51 may be directly connected to the casing 4, which does not deteriorate the effects of the above invention, and there is no particular limitation on the above configuration.

Another means for detecting damage of the deformable plane which is different from that as described above will be explained below with reference to FIG. 24.

As shown in FIG. 23, in measuring a pressure in the liquid flow path 8 by the liquid chamber pressure measuring means 61 and the air chamber pressure measuring means 60, ideally for the pressure sensor, both of the liquid chamber pressure measuring means 61 and the air chamber pressure measuring means 60 measure identical pressures. However, actually, as the pressure in the liquid flow path 8 is increased or decreased, the deformable plane 20 is elongated, and the pressure measured by the liquid chamber pressure measuring means 60 is reduced by the value which is used for the elongation.

Therefore, as shown in FIG. 24, the pressure in the liquid flow path 8 by the liquid chamber pressure measuring means 61 can be shown as a linear line like pressure characteristics 90, but when the same pressure is measured by the air chamber pressure measuring means 60, the pressure less than the pressure characteristics 90 is measured as shown in the pressure characteristics 91. Thus, when the pressure measured by the air chamber pressure measuring means 60 is equal to that measured by the liquid chamber pressure measuring means 61, it is determined that the deformable plane 20 is damaged.

Therefore, any damage of the deformable plane 20 can be detected by the following procedures:

1. Opening the liquid chamber adjusting to atmospheric pressure means 80 and the air chamber adjusting to atmospheric pressure means 81 to pressurize each of the pressure in the liquid chamber 6 and the pressure in the air chamber 9 to atmospheric pressure;
2. Closing liquid chamber adjusting to atmospheric pressure means 80 and the air chamber adjusting to atmospheric pressure means 81; and
3. Determining whether the pressure measured by the air chamber pressure measuring means 60 is equal to the characteristics which is memorized in advance or not, in the process to increase the pressure in the liquid flow path 8 to the pressure P1 or decrease to the pressure P3 by the liquid chamber pressure controlling means 70.

The pressure characteristics 90 measured by the air chamber pressure measuring means 60 vary depending on the shapes and materials of the liquid chamber 6 and the deformable plane 20, but can be measured using the above described method.

In other words, after the change characteristics of the pressure in the air chamber 9 corresponding to the pressure in the liquid chamber 6 is memorized in advance, and the pressures in the air chamber 9 and the liquid chamber 6 are pressurized to atmospheric pressure by the air chamber adjusting to atmospheric pressure means 81 and the liquid chamber adjusting to atmospheric pressure means 80, and the pressure in the liquid chamber 6 is increased or decreased by the liquid chamber pressure controlling means 70, the damage detecting means 5 determines that the deformable plane 20 is damaged when the change in the pressure in the air chamber 9 which corresponds to the change in the pressure in the liquid chamber 6 measured by the liquid chamber pressure measuring means 61 is different from the memorized change characteristics of the pressure in the air chamber 9.

(Detecting of Attachment)

Now, with reference to the drawings, embodiments of a pressure sensor and a connection method thereof according to the present invention will be explained below, but the present invention is not limited to these embodiments.

FIG. 25 is a schematic view showing a pressure sensor according to the present embodiment. A pressure sensor 1 is configured with: the casing 4 which is disposed on the way to the liquid flow path 8, including a liquid chamber 6 having the air chamber 9 with the air inlet/outlet 50, the liquid chamber 6 having the liquid flow inlet 40 and the liquid flow outlet 41, and the deformable plane 20 that is sandwiched between the air chamber 9 and the liquid chamber 6 to separate the air chamber 9 and the liquid chamber 6, and is deformed depending on the difference between the pressure in the air chamber 9 and the pressure in the liquid chamber 6; and air chamber pressure measuring means 60 which is connected to the air inlet/outlet 50 via a communication section 51 which is open to an attachment surface 300, and measures a pressure in the liquid chamber 6 through the deformable plane 20 on the air chamber side; the attachment surface 300 to which the casing 4 is attached; and attachment sensing means 210 for determining the close contact between the casing 4 and the attachment surface 300.

The pressure sensor 1 is disposed on the way to the liquid flow path 8, and measures a pressure in the liquid flow path. When the pressure in the liquid chamber 6 changes, the deformable plane 20 is deformed and the pressure in the air chamber 9 changes in correlation with the pressure in the liquid chamber. The pressure sensor 1 measures a pressure in the air chamber 9 thereby, and converts the value to measure the pressure in the liquid chamber 6. Here, the air inlet/outlet 50 of the casing 4 is in communication with the air chamber pressure measuring means 60 via the communication section 51. The pressure sensor 1 is configured so that when the casing 4 is in contact with the attachment sensing means 210, the communication section 51 and the air inlet/outlet 50 are connected to each other in an air-tight manner.

The connection between the air inlet/outlet 50 and the communication section 51 may be a luer connector, a coupler, a sleeve-shaped tube for insertion, or the like. The connection may be any connections which can connect between the air inlet/outlet 50 and the communication section 51 in air-tight manner, and therefore there is no particular limitation on the above connection.

The attachment sensing means 210, in FIG. 25, is disposed to the attachment surface 300, but may be disposed to the casing 4, which does not deteriorate the above described effects. However, since the casing 4 is generally a disposable product as described above, the disposition of expensive components such as the attachment sensing means is disadvantageous in terms of cost. Therefore, the attachment sensing means 210 is preferably attached to the attachment surface 300. The attachment sensing means 210 may be any device which can detect the bonding between the casing 4 and the attachment surface 300. For example, a microswitch and a hole element may be used, but there is no particular limitation on them. In FIG. 25, the attachment sensing means 210 is disposed on the surface of the attachment surface 300, and is described as being in contact with the surface of the air chamber 9 of the casing 4. However, the attachment sensing means 210 may be disposed anywhere as far as the above effects are not deteriorated and there is no particular limitation on the position.

In FIG. 25, the casing 4 is attached to the attachment surface 300 at an angle of 90 degrees. For example, as shown in FIG. 26, the angle may be 70 degrees. The casing 4 is desirably attached at an angle of from 70 to 90 degrees, more desirably from 80 to 90 degrees, and most desirably at an angle of 90 degrees in terms of processability of the casing 4 and the attachment surface 300. In FIG. 25, both of the attachment surface of the casing 4 and the attachment surface 300 are flat. However, both surfaces may have any shape that can connect the air inlet/outlet 50 and the communication section 51 in an air-tight manner, and may have an undulated shape or a sinusoidal wavy shape for example. In any case, the effects of the above invention are not deteriorated, and there is no particular limitation on the shape.

In the pressure sensor 1, the casing 4 and the attachment surface 300 are bonded to each other only at air inlet/outlet 50 and the communication section 51 in FIG. 25. As shown in FIG. 27, the casing 4 is more desirably provided with a fixture 220. A fixing of the casing 4 with the fixture 220 enables a measurement of pressure during a therapy without any falling of the casing 4 from the attachment surface 300. The fixture 220 is disposed to the attachment surface 300 in FIG. 27. However, the fixture 220 may be disposed to the casing 4 side, which does not deteriorate the above effects, and there is no particular limitation on the position. The fixture 220 may be any device that can prevent the casing 4 from falling off from the attachment surface 300, and there is no limitation on the shape of the device.

In FIG. 25, the casing 4 and the air chamber pressure measuring means 60 are directly connected to the communication section 51 through the air inlet/outlet 50. However, as shown in FIG. 28, the air inlet/outlet 50 may be provided with a guide tube 54 having a communication section connection port 53 at the tip thereof, so that the part of the communication section connection port 53 and the communication section 51 can be connected to each other. In this case, there is no problem as long as the attachment sensing means 210 can detect the connection between the communication section connection port 53 and the attachment surface 300. Not shown in FIG. 28, but the communication section attachment port 53 is desirably fixed with a fixture like that shown in FIG. 27. The communication section connection port 53 may have a shape similar to that of the air inlet/outlet 50 described in the explanation of FIG. 25. In addition the attachment sensing means 210 may be disposed to the communication section connection port 53, which does not deteriorate the above effects.

In FIG. 27, the casing 4 is attached to the fixture 220 by attaching the casing 4 in a direction perpendicular to the attachment surface. However, as shown in FIG. 29, even if the fixing means in which the casing 4 is inserted in the fixture 220 having a hook shape and rotated along the attachment surface 300 for fixing is used, the above effects are not deteriorated, and therefore there is no particular limitation on the position.

Also as shown in FIG. 30, attachment sensing means 210 may be provided at the end of the rotation of the casing 4, which does not deteriorate the above effects, and there is no particular limitation on the position. Here, since casing 4 is disposed on the way to the liquid flow path 8, the rotation of the casing 4 requires the rotation of the whole liquid flow path 8.

Therefore, this needs significant labor. Thus, as shown in FIG. 31, if the casing 4 is disposed to be surrounded by a rotating body 240, the disposition as that shown in FIGS. 29 and 30 can be done without the rotation of the casing 4.

In using the attachment methods as shown FIG. 25 to FIG. 31, there is not a play between the air inlet/outlet 50 or the communication section connection port 53 and the communication section 51, and the manufacturing error needs to be minimized as much as possible. Thus, as shown in FIG. 32, the communication section 51 may have a cushioning section 250 at the tip thereof to provide a margin for the size of the connection.

The cushioning section 250 may be any device that moves in a direction toward the connection of the casing 4 and applies a force toward the casing 4. As an example, the one using a reaction force of a spring may be used, but there is no particular limitation on it. It is more preferable to dispose a moving guide 260 in order to limit the moving direction of the cushioning section 250 to the direction toward the connection of the casing 4.

Here, the fixture 220 and the rotating body 240 may be formed of synthetic resin, metal, glass, or the like, but is preferably formed of a hard material from the viewpoint of operability. Also from the viewpoint of manufacturing cost, processability and operability, synthetic resin, particularly thermoplastic resin is preferred. The thermoplastic resin includes polyolefin resin, polyamide resin, polyester resin, polyurethane resin, fluoro resin, silicon resin, and the like, and also includes ABS (acrylonitrile-butadiene-styrene copolymer) resin, polyvinyl chloride, polycarbonate, polystyrene, polyacrylate, polyacetal, and the like, and any of these can be preferably used.

EXAMPLE

Now, the following is the explanation of a confirmation of effect obtained by the present invention by way of the examples. The pressure sensors having the configuration shown in FIG. 1 (first embodiment) and FIG. 34 (comparative example 1) were used to perform a comparative test about displacement efficiency of liquid, by the following method:
(1) Tap water which was colored to orange-red was used as a first liquid that flows through the liquid flow path 8 and the pressure sensor 1, and a liquid feed pump was used to supply the tap water at a rate of 50 ml/min to fill the liquid flow path 8 and the pressure sensor 1;
(2) Next, clear tap water was used as a second liquid that flows through the liquid flow path 8 and the pressure sensor 1, and a liquid feed pump was used to supply the tap water at the same rate of 50 ml/min; and
(3) The period of time from when the supplying of the second liquid was started until the water in the casing of the pressure sensor 1 became clear, that is until the water in the casing was displaced with clear tap water, was measured.

First Embodiment

The liquid flow path 8 was provided by individually connecting tubes of soft polyvinyl chloride having an inner diameter of 3.3 mm to the inlet side and the outlet side of the pressure sensor 1, and placing a peristaltic pump on the circuit on the inlet side as a feed pump. A test was performed using the reference plane 10 and the deformable plane 20 having a diameter of 20 mm, the liquid flow path 8 of FIG. 1 with the first connecting plane having a height of 10 mm, and the pressure sensor 1. The reference plane 10, the deformable plane 20, and the connecting plane 11 were individually formed of polycarbonate. Because the purpose of the test was to measure displacement efficiency and no measurement of pressure was performed, the deformable plane 20 was entirely formed of polycarbonate, and no section which is deformable (deformable section) was provided thereto. As a result of the test, it required 120 seconds to displace the water in the casing with clear tap water.

Comparative Example 1

To the contrary, in the comparative example 1, the test similar to that in the first embodiment was performed using the pressure sensor of FIG. 34 having the same size as that in the first embodiment in which the liquid flow inlet 40 and the liquid flow outlet 41 are disposed substantially in-line with each other, and as a result of that it required 450 seconds to displace the water in the casing with clear tap water.

(Result of Comparison)

The above results showed that an arrangement which causes a fluid to be introduced into a casing having the liquid flow inlet 40 and the liquid flow outlet 41 provided in the connecting plane 12 to flow along the inner circumference of the connecting plane 12 provides an outstanding effect to prevent retention of the body fluid or medicinal solution in the casing.

INDUSTRIAL APPLICABILITY

A pressure sensor of the present invention is almost free from the risk to cause coagulation of body fluid, and so is able to safely measure a pressure in an extracorporeal circulating circuit during an extracorporeal circulation therapy in which blood is pulled out of the body of a patient for an extracorporeal treatment by a blood processing apparatus and the blood is returned into the body after the treatment. Therefore, a pressure sensor of the present invention is able to be usefully used in extracorporeal circulation treatment. Also, a pressure sensor of the present invention is able to detect a liquid pressure with little measurement error without any contact between the liquid and air. Thus, in an extracorporeal circulation therapy in which blood is pulled out of the body of a patient for an extracorporeal treatment by a blood processing apparatus and the blood is returned into the body after the treatment, a pressure sensor of the present invention can safely measure a pressure in an extracorporeal circulating circuit. Therefore, a pressure sensor of the present invention can be usefully used in extracorporeal circulation treatment.

Moreover, a pressure sensor of the present invention is able to detect damage of the flexible diaphragm of the pressure sensor, and ensures safety as a pressure sensor. Thus, in an extracorporeal circulation therapy in which blood is pulled out of the body of a patient for an extracorporeal treatment by a blood processing apparatus and the blood is returned into the body after the treatment, a pressure sensor of the present invention can safely measure a pressure in an extracorporeal circulating circuit. Therefore, a pressure sensor of the present invention can be usefully used in extracorporeal circulation treatment. Furthermore, a pressure sensor of the present invention surely detects the connection between a casing of the pressure sensor and an attachment surface. Thus, in an extracorporeal circulation therapy in which blood is pulled out of the body of a patient for an extracorporeal treatment by a blood processing apparatus and the blood is returned into the body after the treatment, a pressure sensor of the present invention can safely measure a pressure in an extracorporeal circulating circuit. Therefore, a pressure sensor of the present invention can be usefully used in extracorporeal circulation treatment.

BRIEF DESCRIPTION OF THE DRAWINGS

FIG. 19 is a schematic view showing further another embodiment of a pressure sensor according to the present invention;

FIG. 20 is a schematic view showing further another embodiment of a pressure sensor according to the present invention;

Figure 1:
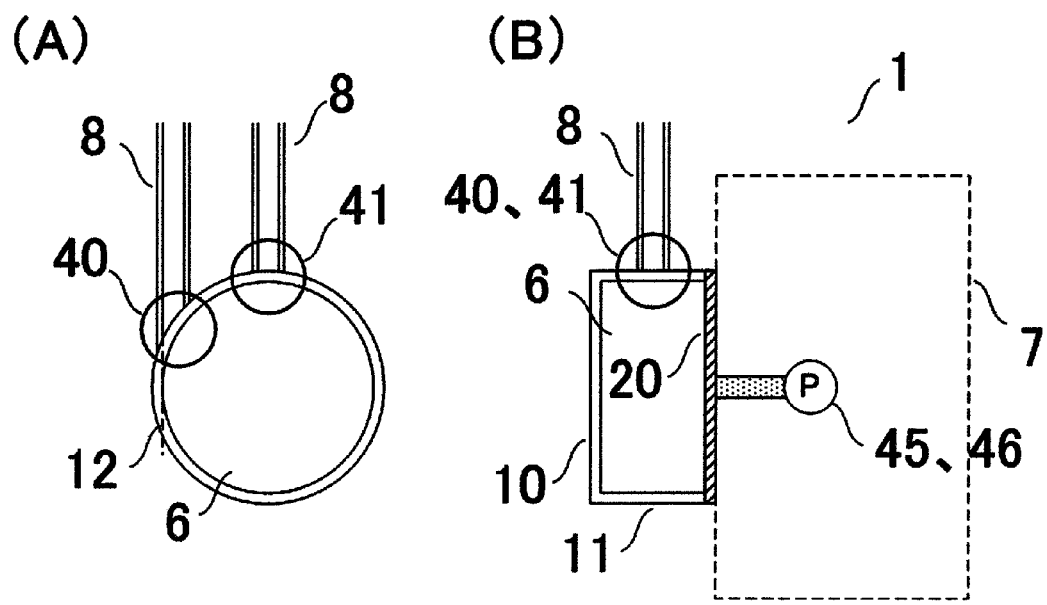
FIG. 1(A) is a schematic front view and FIG. 1(B) is a schematic side view showing one embodiment of a pressure sensor according to the present invention.
Figure 2:
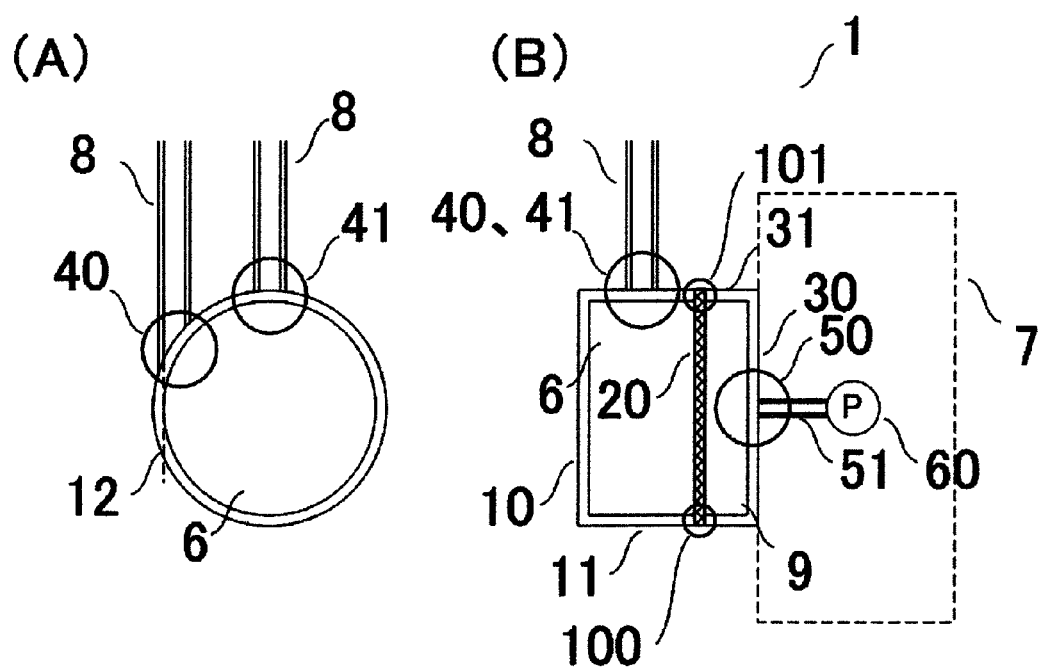
FIG. 2(A) is a schematic front view and FIG. 2(B) is a schematic side view showing another embodiment of a pressure sensor according to the present invention.
Figure 3:
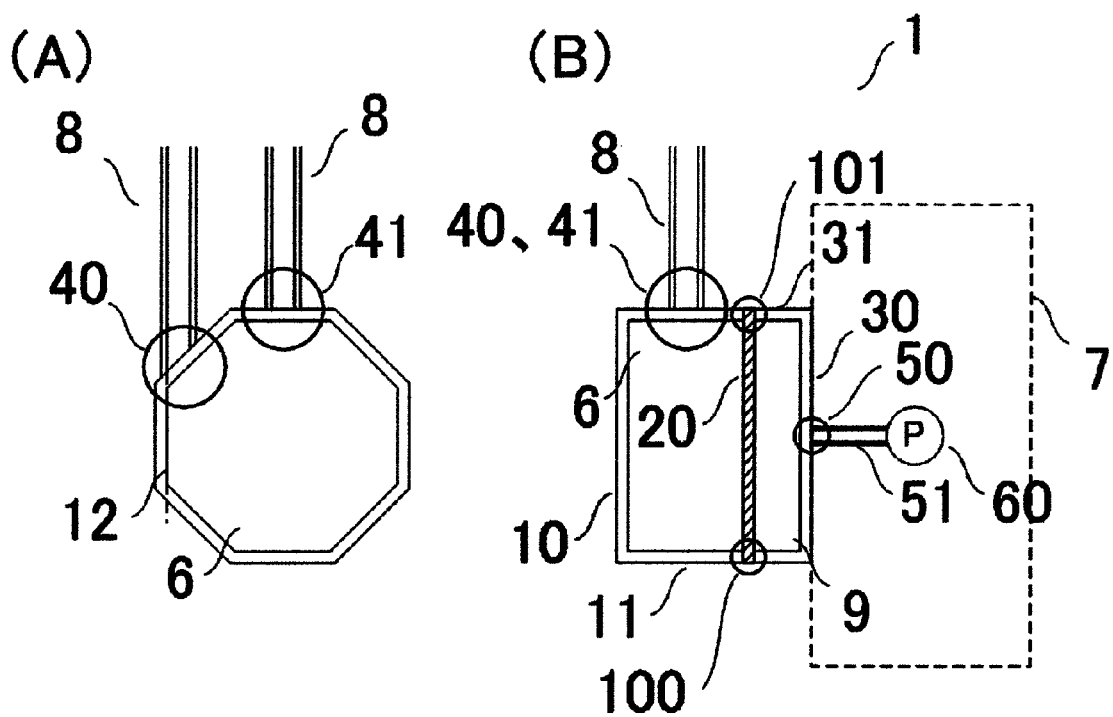
FIG. 3(A) is a schematic front view and FIG. 3(B) is a schematic side view showing further another embodiment of a pressure sensor according to the present invention.
Figure 4:
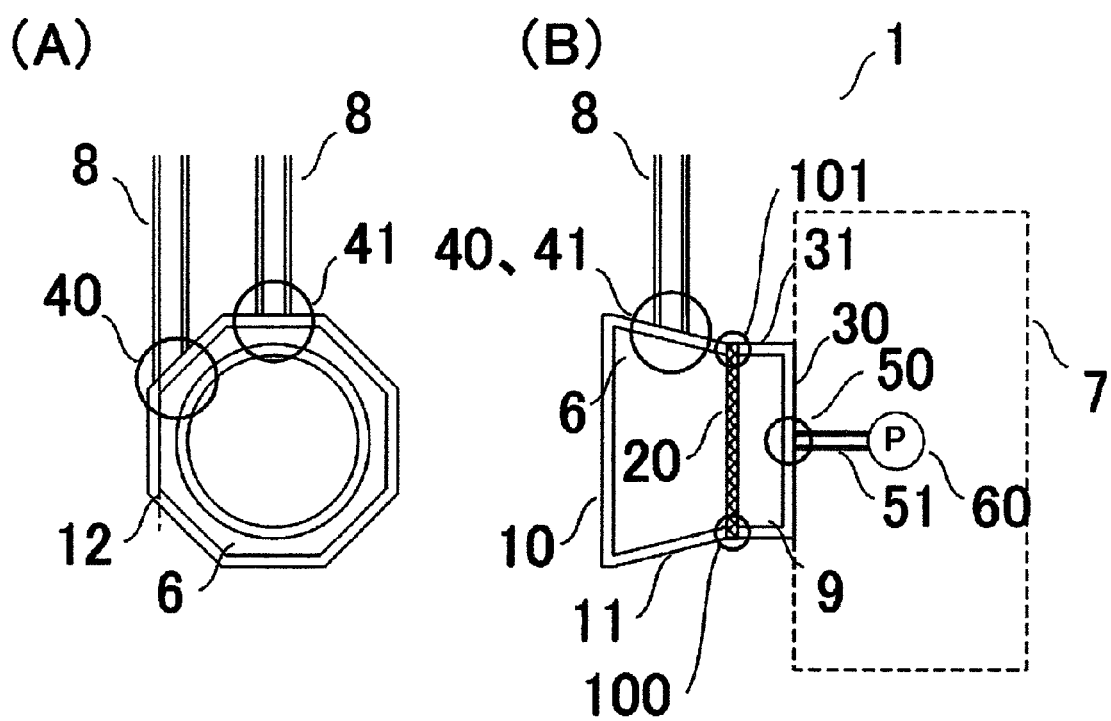
FIG. 4(A) is a schematic front view and FIG. 4(B) is a schematic side view showing further another embodiment of a pressure sensor according to the present invention.
Figure 5:
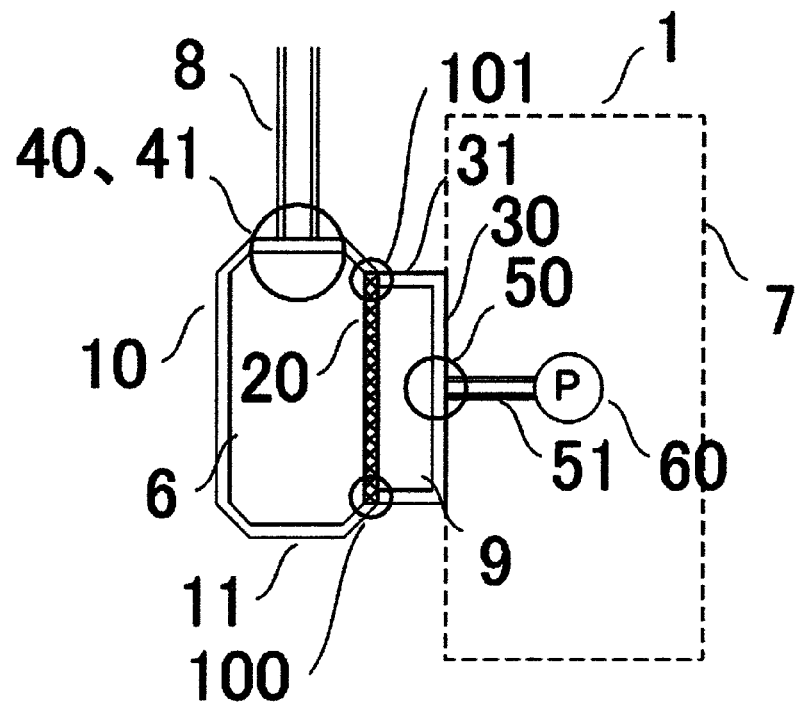
FIG. 5 is a schematic view showing further another embodiment of a pressure sensor according to the present invention.
Figure 6:
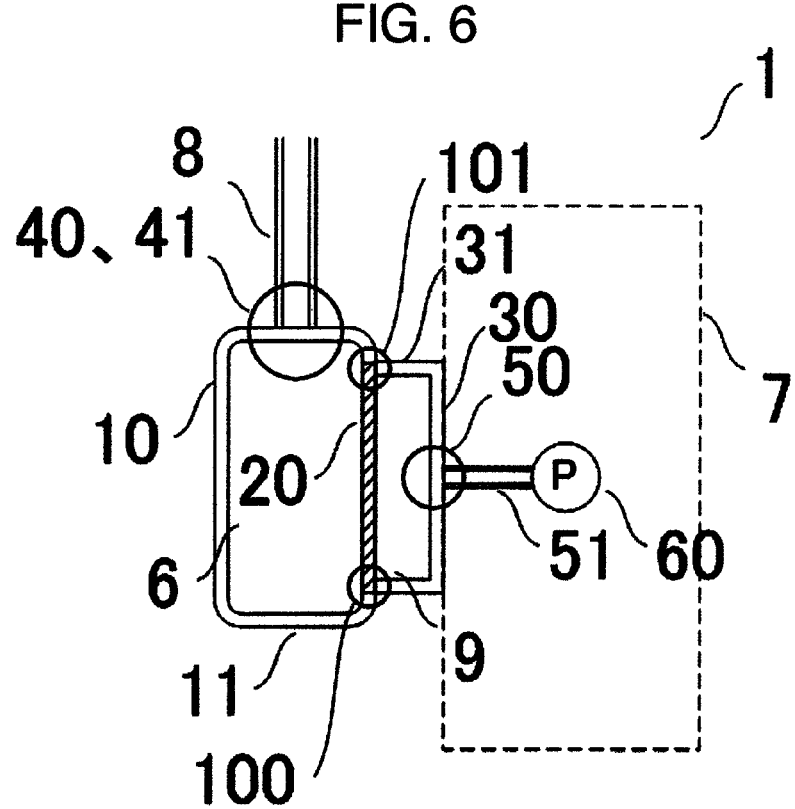
FIG. 6 is a schematic view showing further another embodiment of a pressure sensor according to the present invention.
Figure 7:
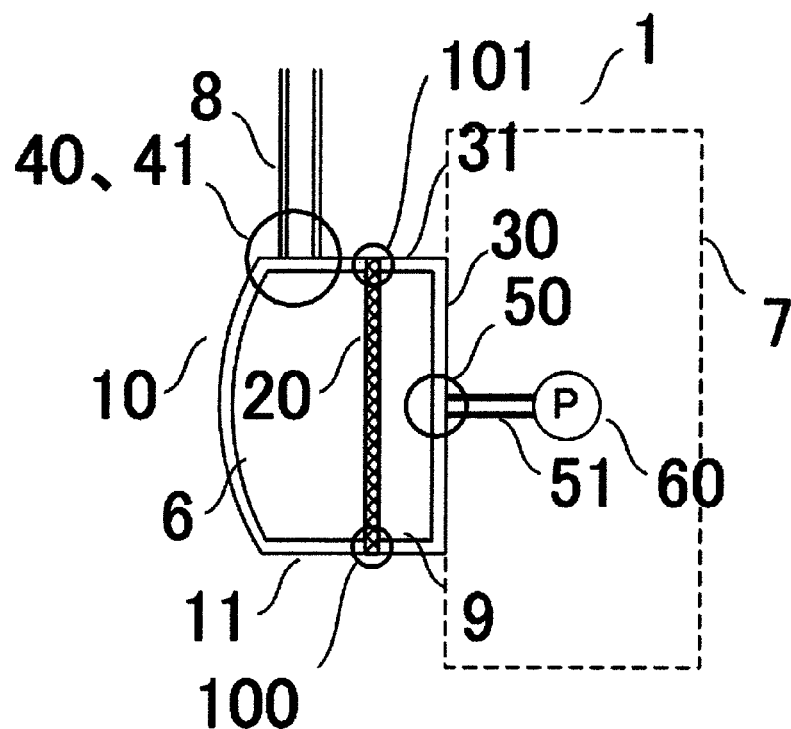
FIG. 7 is a schematic view showing further another embodiment of a pressure sensor according to the present invention.
Figure 8:
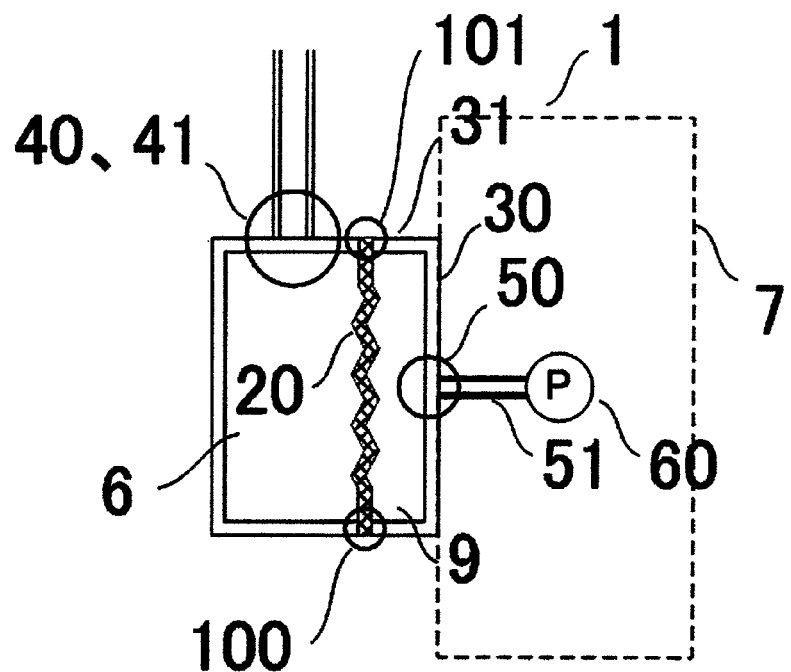
FIG. 8 is a schematic view showing further another embodiment of a pressure sensor according to the present invention.
Figure 9:
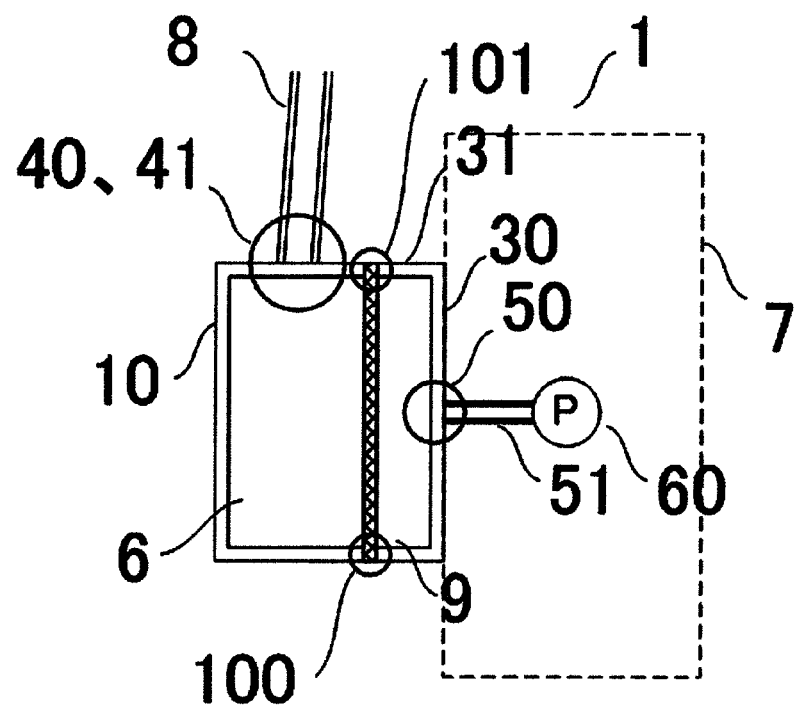
FIG. 9 is a schematic view showing further another embodiment of a pressure sensor according to the present invention.
Figure 10:
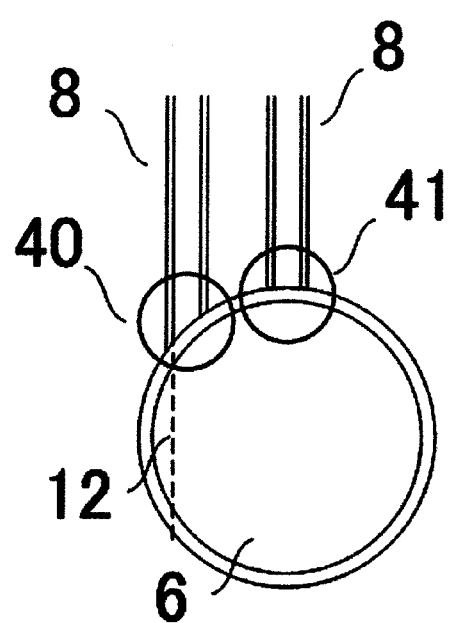
FIG. 10 is a schematic view showing further another embodiment of a pressure sensor according to the present invention.
Figure 11:
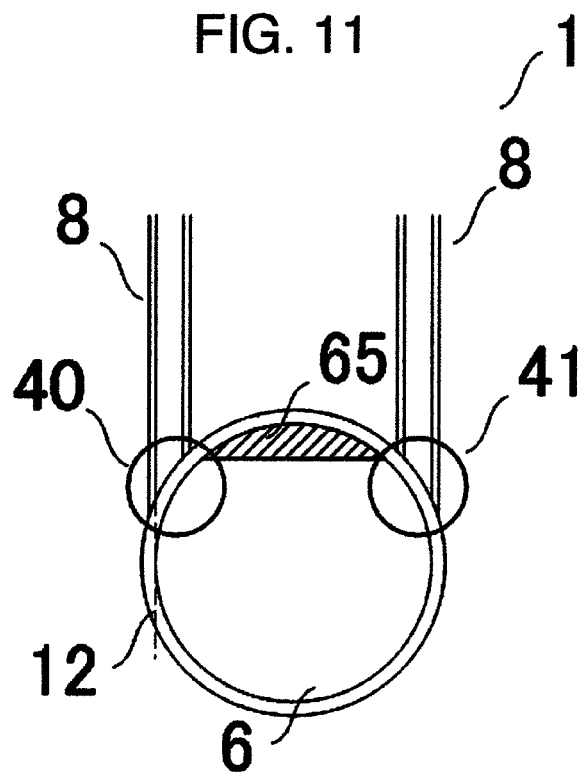
FIG. 11 is a schematic view showing further another embodiment of a pressure sensor according to the present invention.
Figure 12:
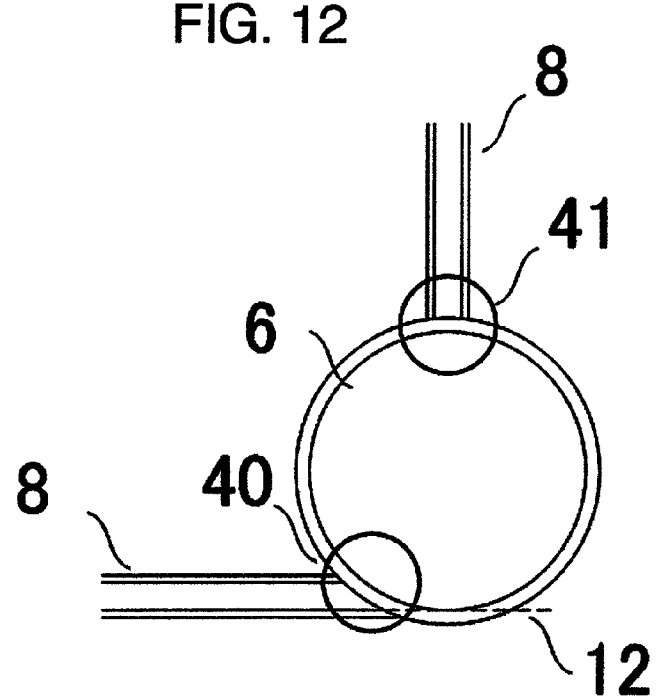
FIG. 12 is a schematic view showing further another embodiment of a pressure sensor according to the present invention.
Figure 13:
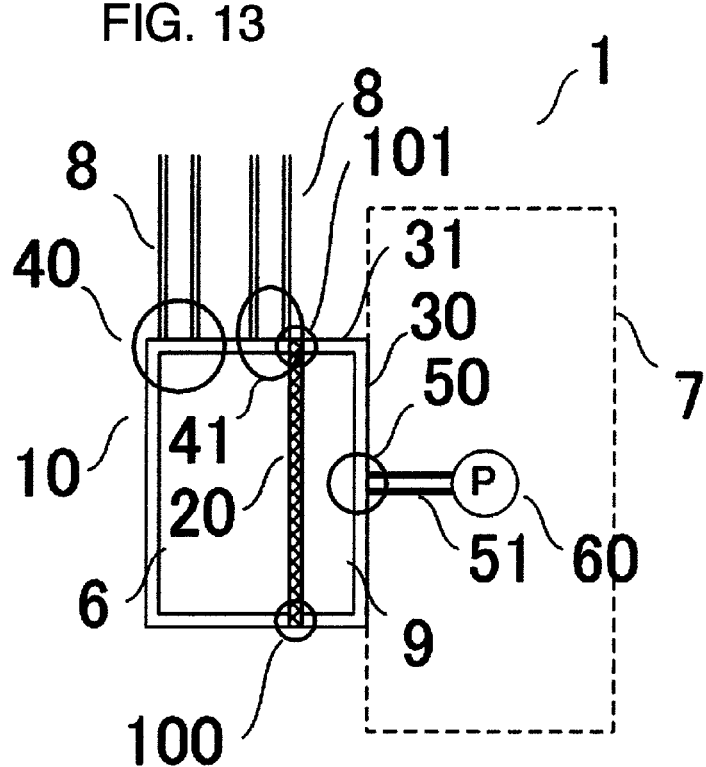
FIG. 13 is a schematic view showing further another embodiment of a pressure sensor according to the present invention.
Figure 14:
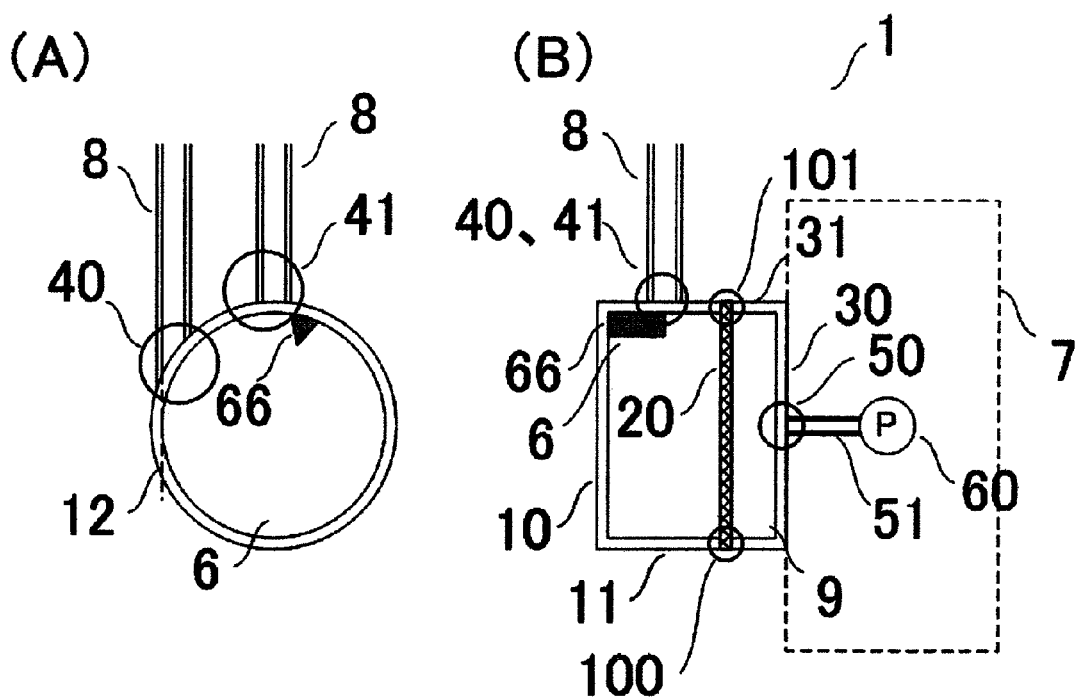
FIG. 14(A) is a schematic front view and FIG. 14(B) is a schematic side view showing further another embodiment of a pressure sensor according to the present invention.
Figure 15:
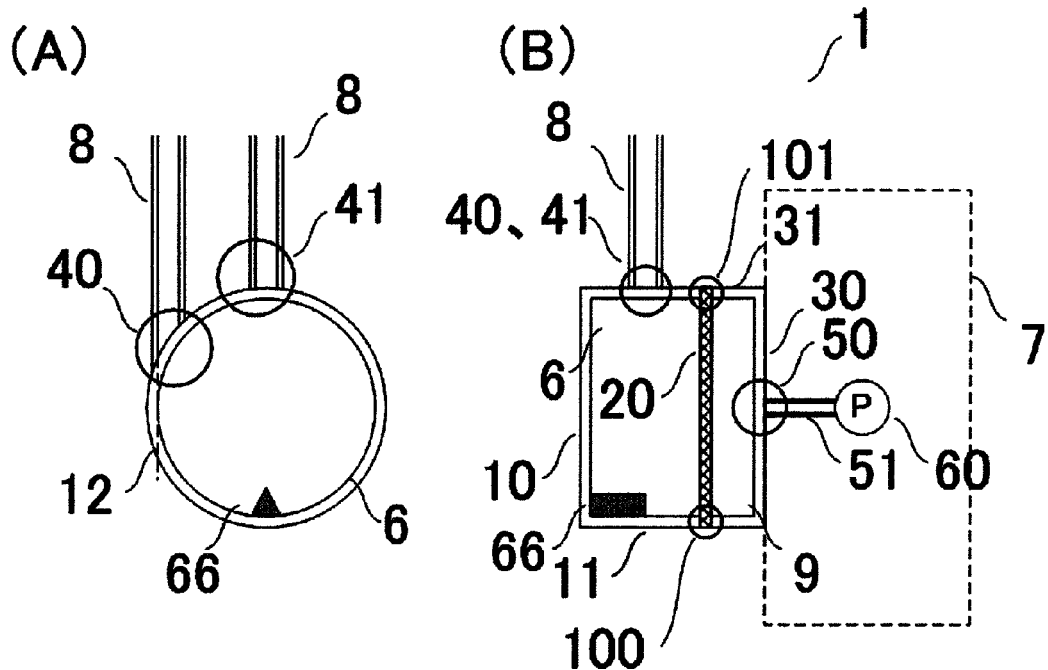
FIG. 15(A) is a schematic front view and FIG. 15(B) is a schematic side view showing further another embodiment of a pressure sensor according to the present invention.
Figure 16:
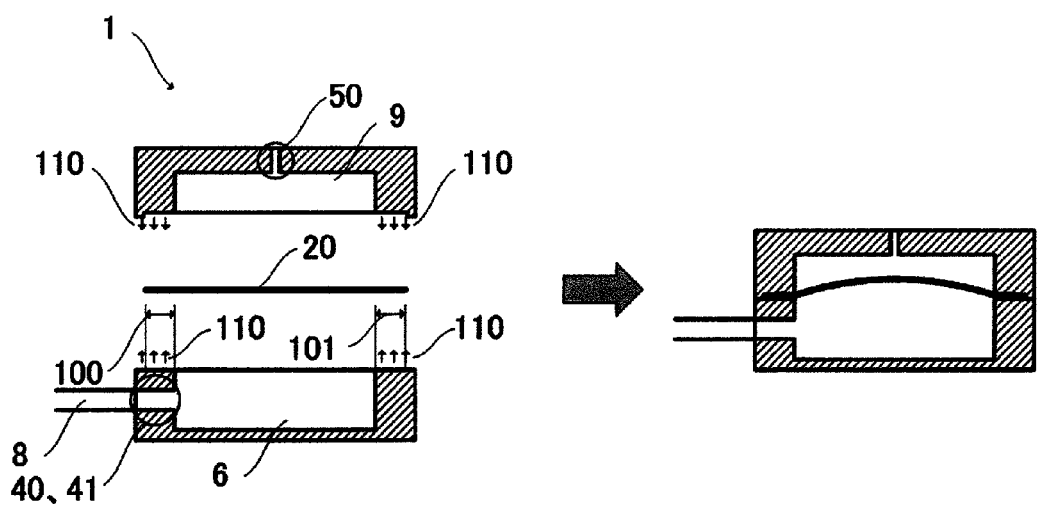
FIG. 16 is a schematic view showing further another embodiment of a pressure sensor according to the present invention.
Figure 17:
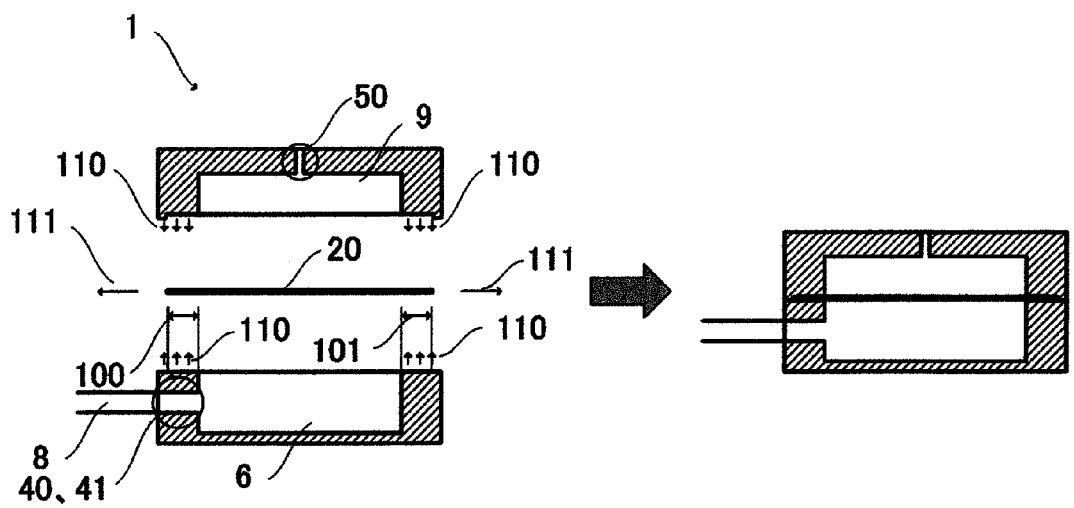
FIG. 17 is a schematic view showing further another embodiment of a pressure sensor according to the present invention.
Figure 18:
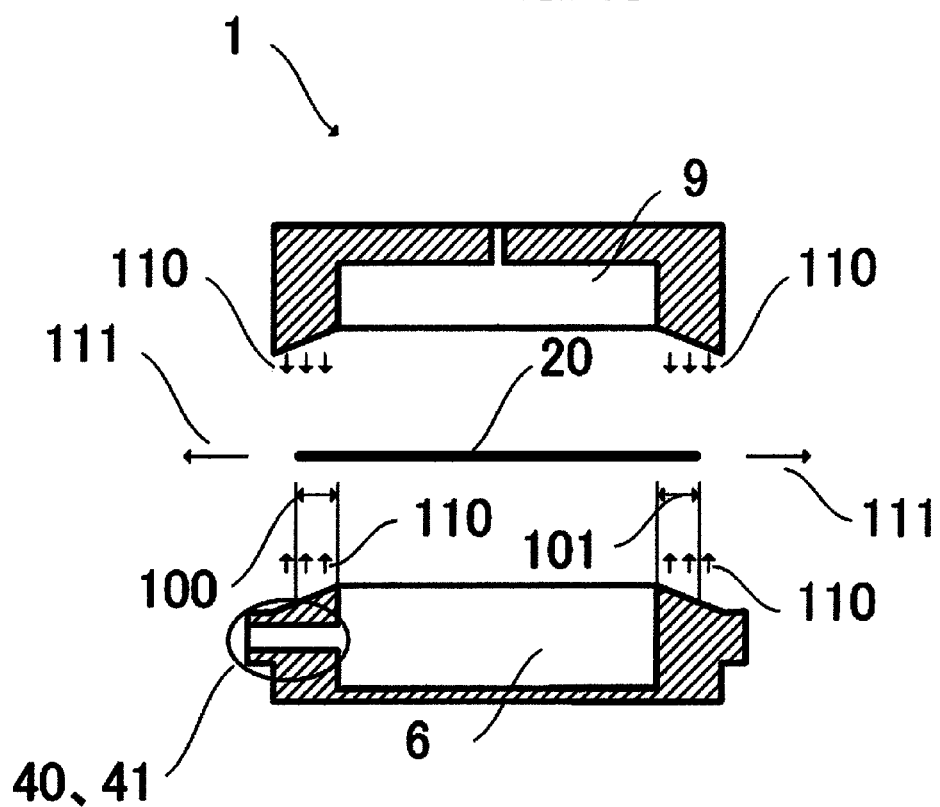
FIG. 18 is a schematic view showing further another embodiment of a pressure sensor according to the present invention.
Figure 21:
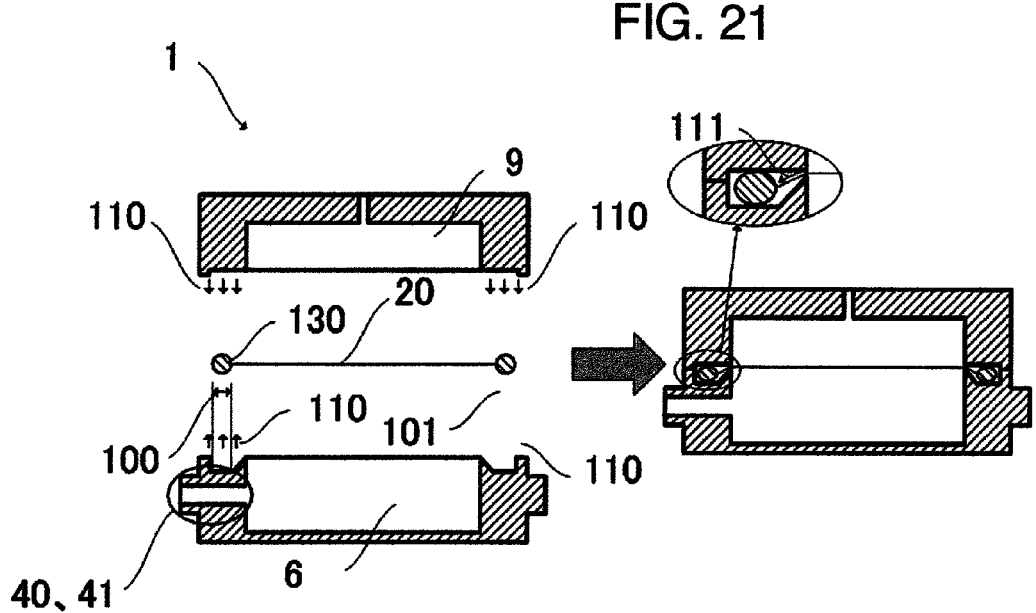
FIG. 21 is a schematic view showing further another embodiment of a pressure sensor according to the present invention.
Figure 22:
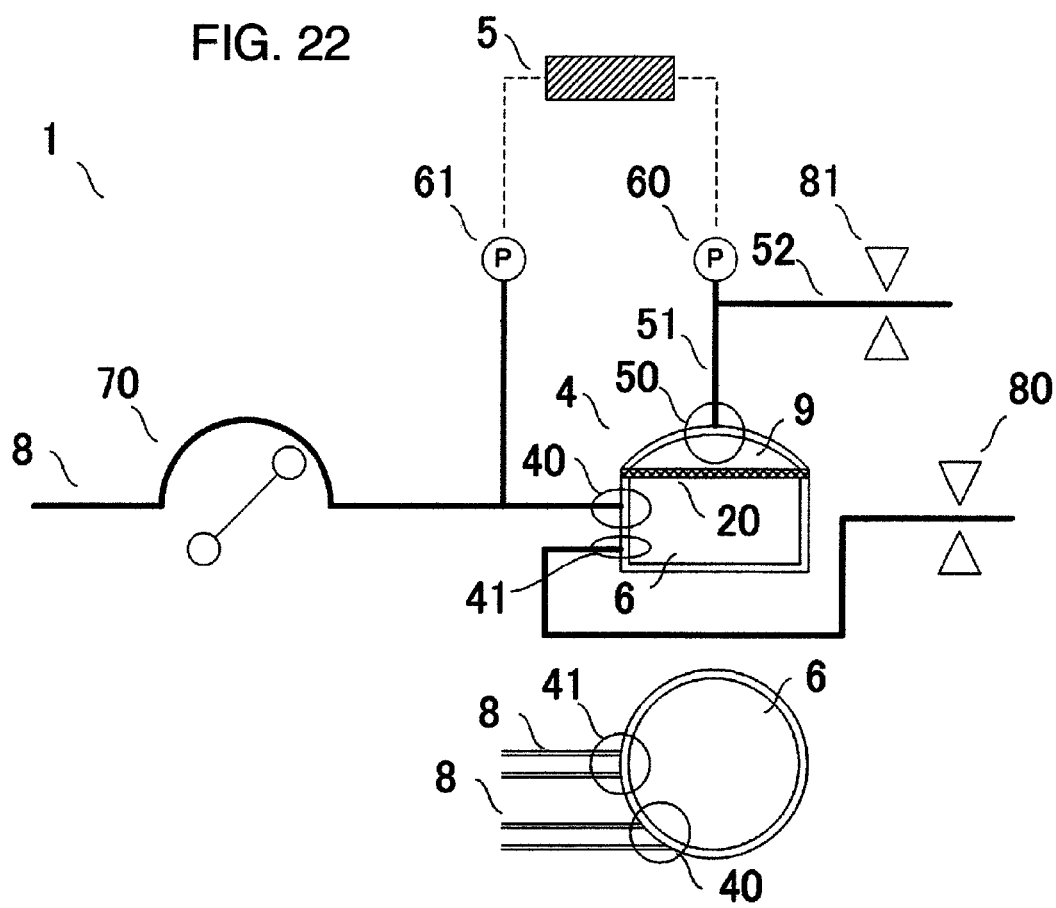
FIG. 22 is a schematic view showing further another embodiment of a pressure sensor according to the present invention.
Figure 23:
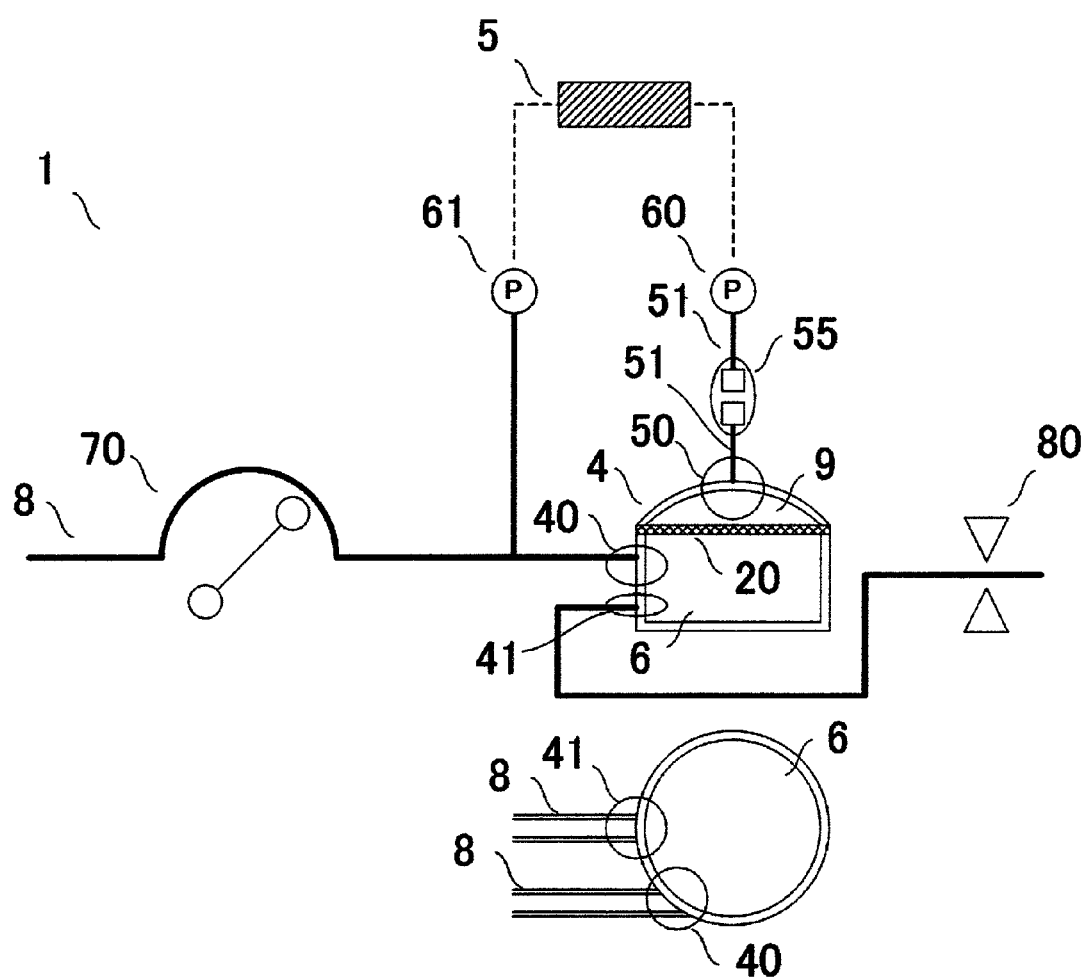
FIG. 23 is a schematic view showing further another embodiment of a pressure sensor according to the present invention.
Figure 24:
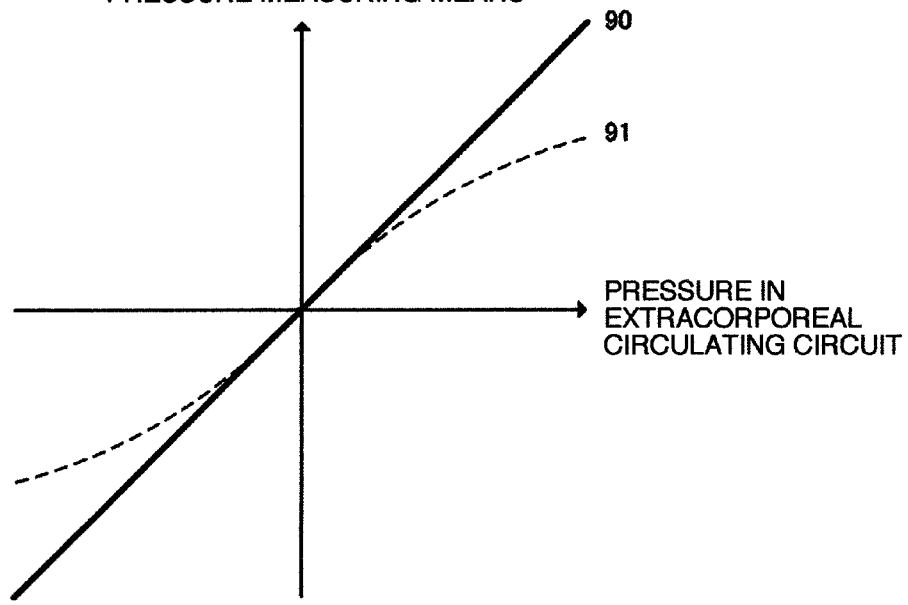
FIG. 24 is a schematic graph showing pressure characterisitics measured by liquid chamber pressure measuring means or air chamber pressure measuring means.
Figure 25:
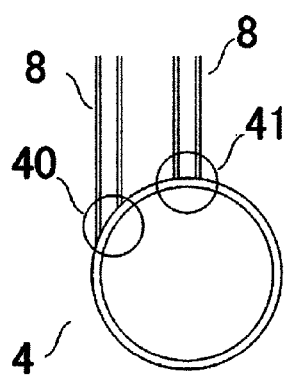
FIG. 25(A) is a schematic front view and FIG. 25(B) is a schematic side view showing another embodiment of a pressure sensor according to the present invention.
Figure 25:
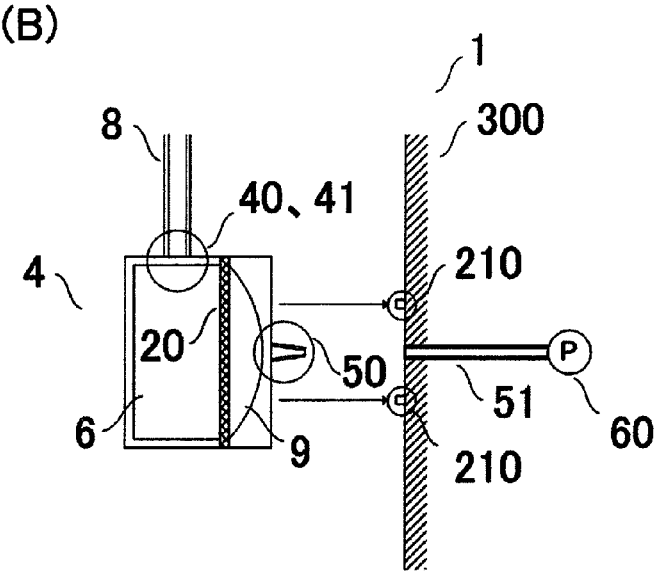
Figure 26:
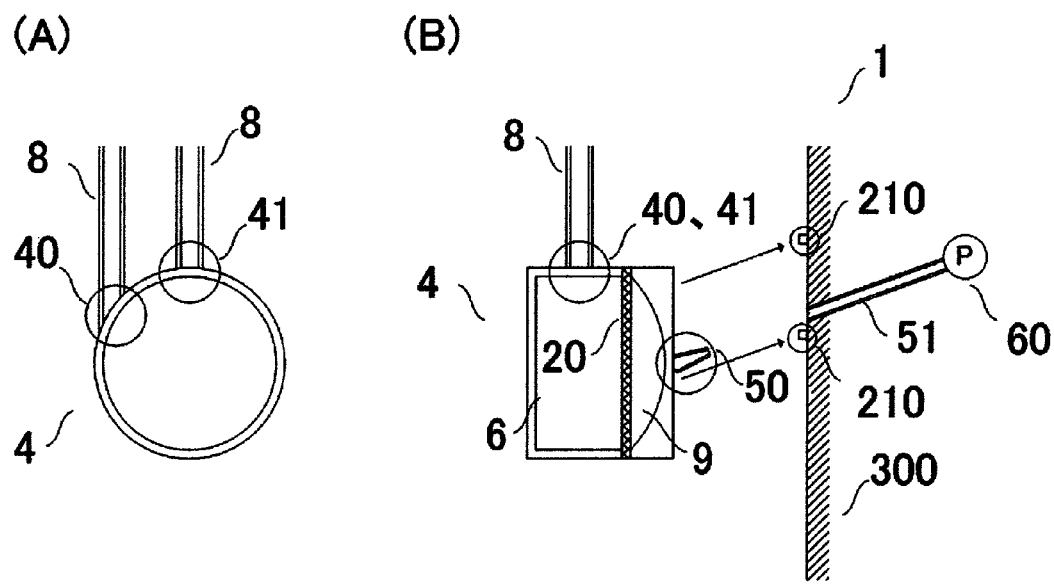
FIG. 26(A) is a schematic front view and FIG. 26(B) is a schematic side view showing another embodiment of a pressure sensor according to the present invention.
Figure 27:
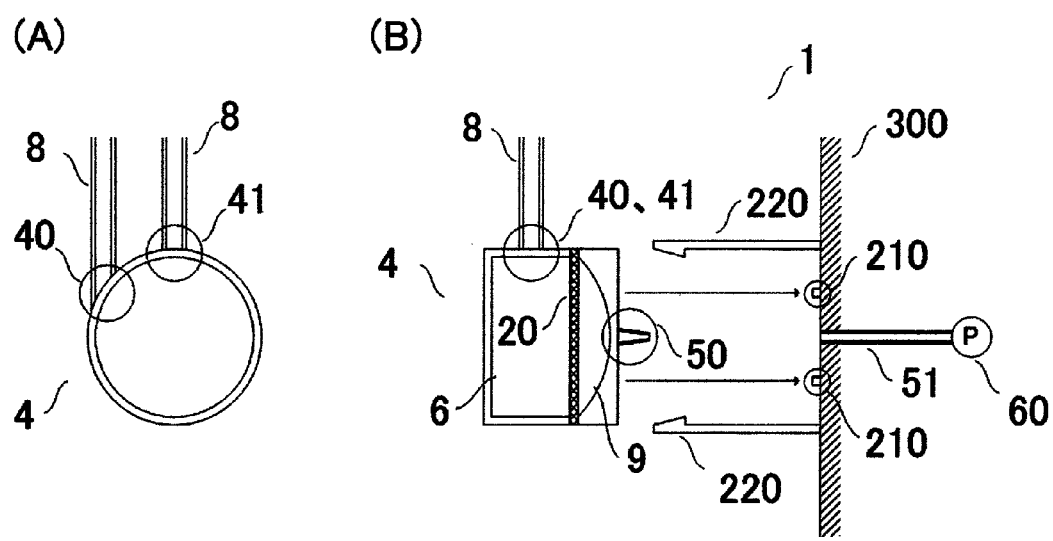
FIG. 27(A) is a schematic front view and FIG. 27(B) is a schematic side view showing another embodiment of a pressure sensor according to the present invention.
Figure 28:
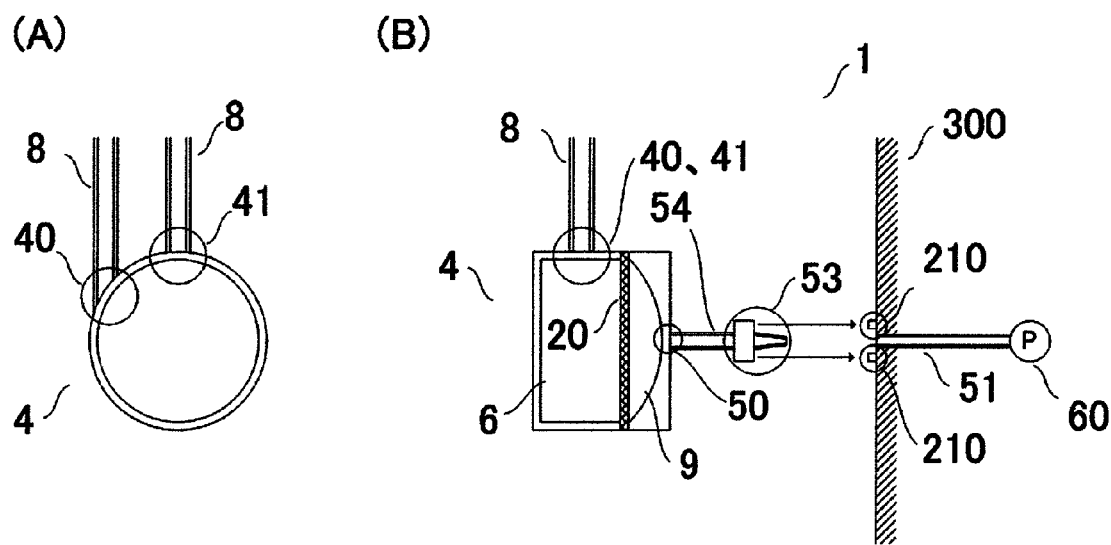
FIG. 28(A) is a schematic front view and FIG. 28(B) is a schematic side view showing another embodiment of a pressure sensor according to the present invention.
Figure 29:
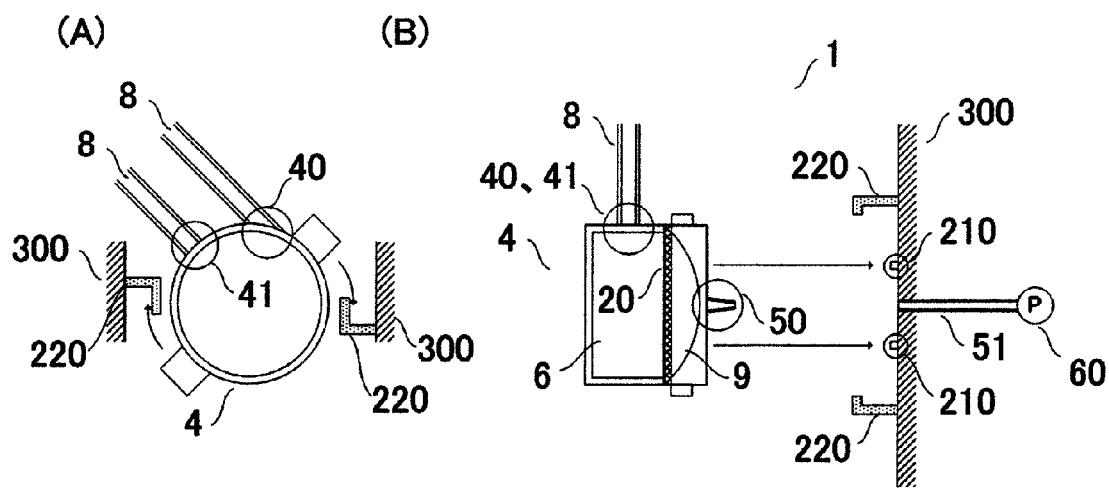
FIG. 29(A) is a schematic front view and FIG. 29(B) is a schematic side view showing another embodiment of a pressure sensor according to the present invention.
Figure 30:
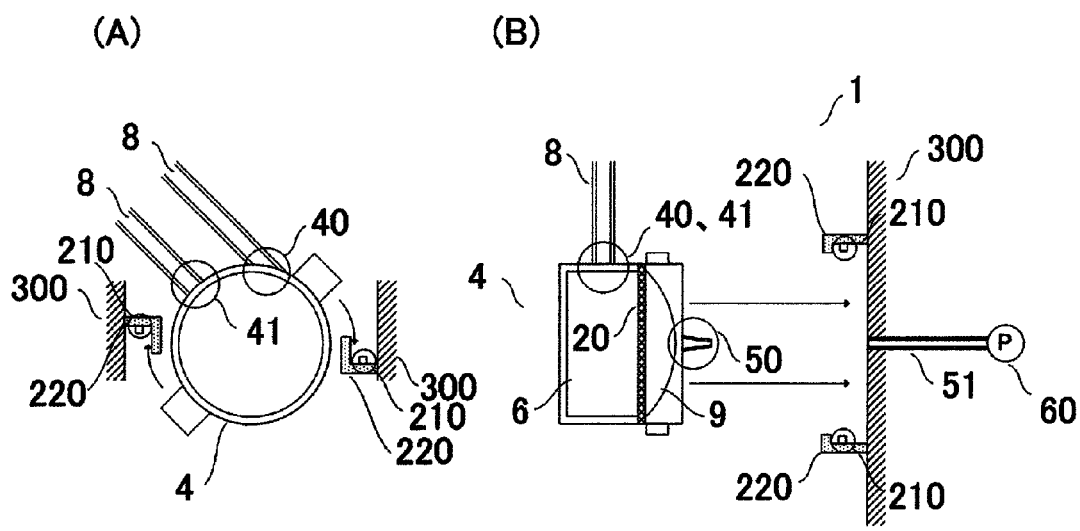
FIG. 30(A) is a schematic front view and FIG. 30(B) is a schematic side view showing another embodiment of a pressure sensor according to the present invention.
Figure 31:
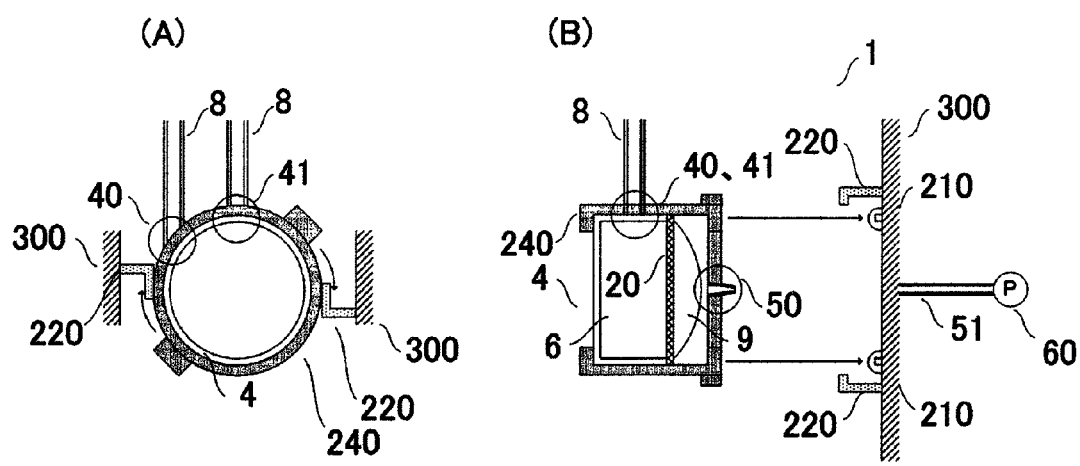
FIG. 31(A) is a schematic front view and FIG. 31(B) is a schematic side view showing another embodiment of a pressure sensor according to the present invention.
Figure 32:
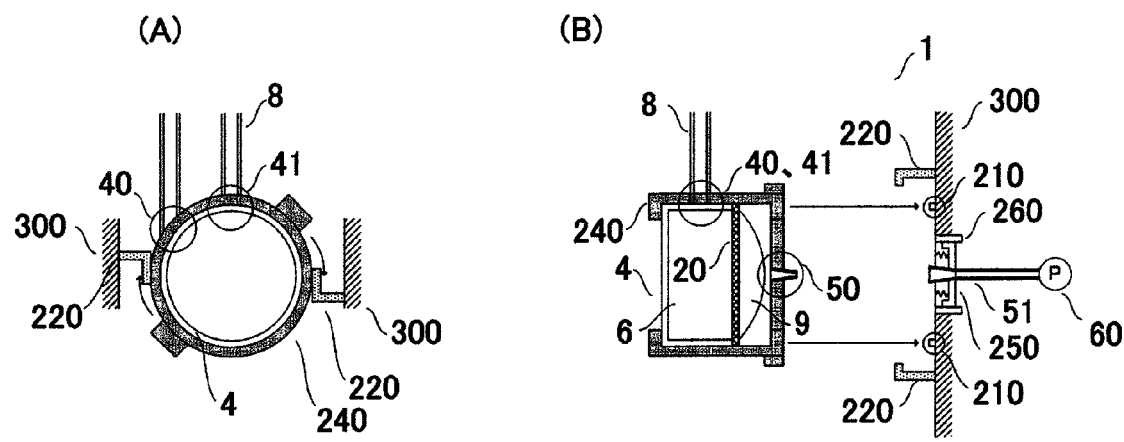
FIG. 32(A) is a schematic front view and FIG. 32(B) is a schematic side view showing another embodiment of a pressure sensor according to the present invention.
Figure 33:
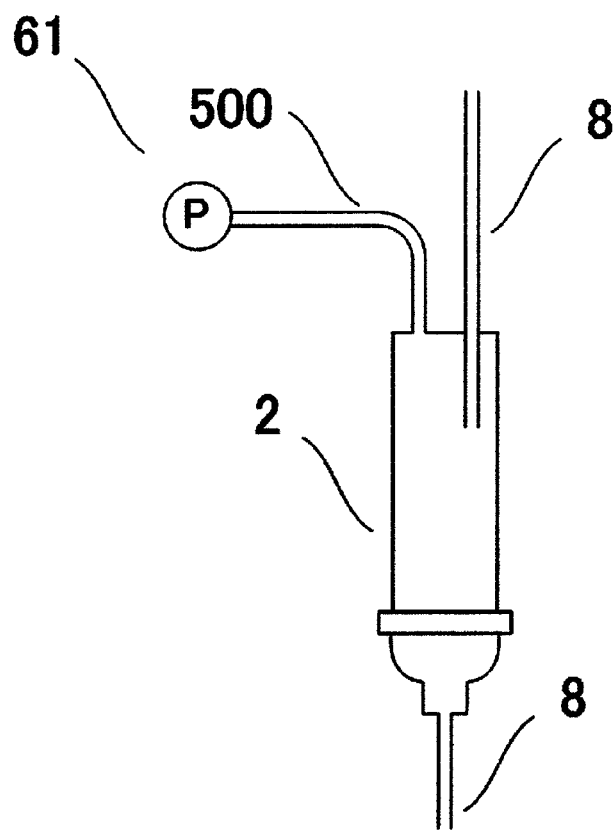
FIG. 33 is a schematic view showing a pressure sensor in the prior art.
Figure 34:
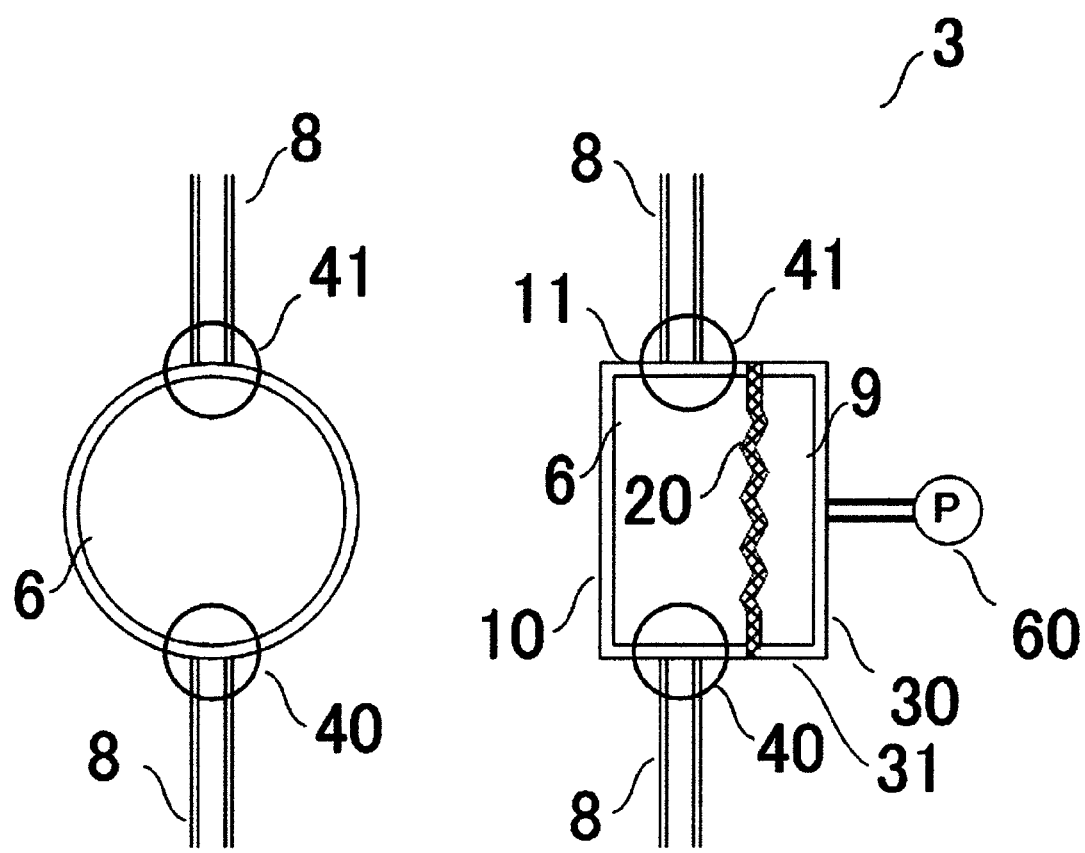
FIG. 34 is a schematic view showing a pressure sensor in the prior art.
Figure 35:
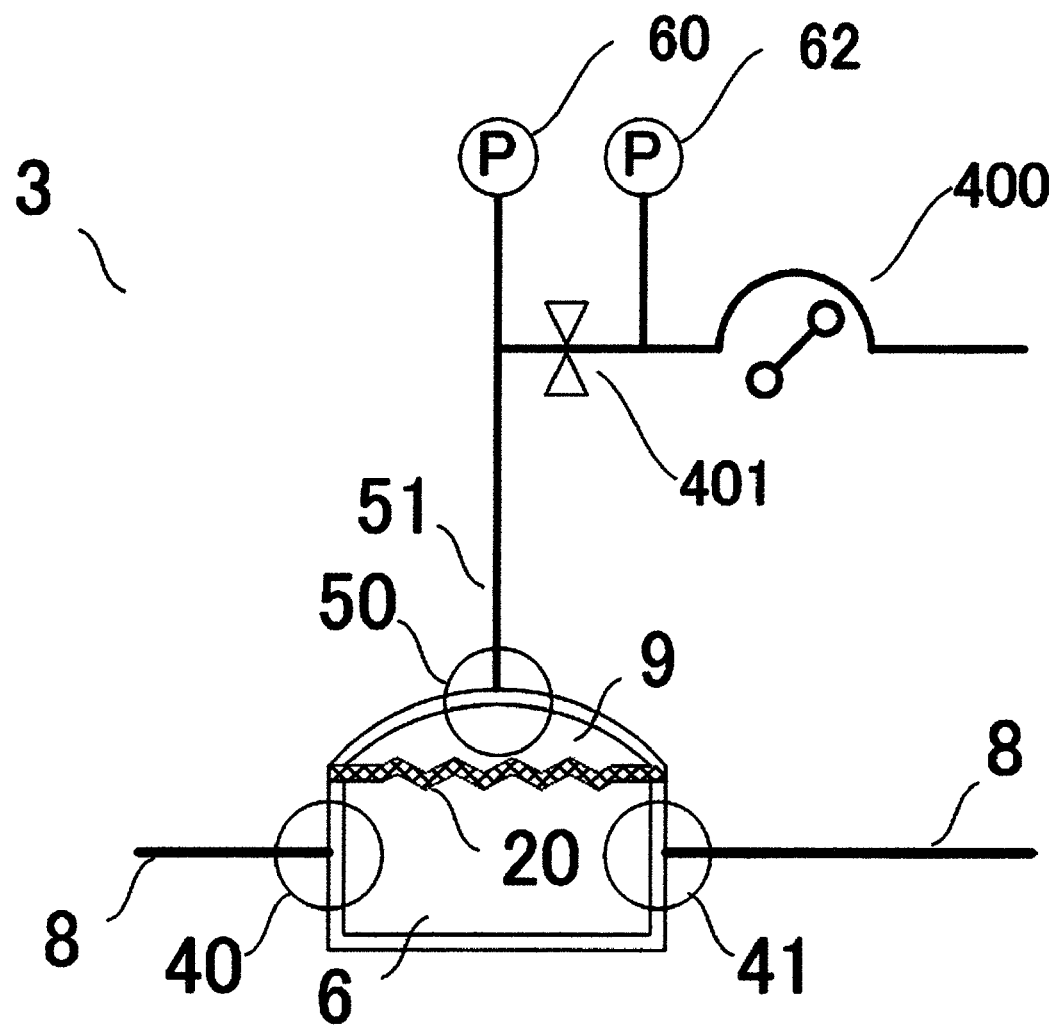
FIG. 35 is a schematic view showing a pressure sensor in the prior art.

DESCRIPTION OF REFERENCE NUMERALS 1 pressure sensor
2 drip chamber
3 pressure sensor in the prior art
4 casing
5 damage detecting means for detecting damage of deformable plane
6 liquid chamber
7 pressure measuring means
8 liquid flow path
9 air chamber
10 reference plane
11 first connecting plane
12 tangential plane to inner surface of liquid flow path 8
20 deformable plane
30 opposing plane
31 second connecting plane
40 liquid flow inlet
41 liquid flow outlet
45 load cell
46 strain gauge
50 air inlet/outlet
51 communication section
52 branched line of communication section
53 connection port of communication section
54 guide tube
55 connecting means of communication section
60 air chamber pressure measuring means
61 liquid chamber pressure measuring means
62 second pressure measuring means
65 region
66 baffle plate
70 liquid chamber pressure controlling means
80 liquid chamber adjusting to atmospheric pressure means
81 air chamber adjusting to atmospheric pressure means
90 pressure characteristics measured by liquid chamber pressure measuring means 61
91 pressure characteristics measured by air chamber pressure measuring means 60
100 sealing portion
101 sealing portion
110 direction of compression
130 ring section
111 direction to which tensile stress is applied
120 surface texture of portion for mechanical seal
210 attachment sensing means
220 fixture
240 rotating body
250 cushioning section
260 moving guide
300 attachment surface
400 pump
401 valve
500 branch tube

The invention claimed is:

1. A pressure sensor for an extracorporeal circulating circuit comprising: a liquid chamber, a pressure measuring means, and a liquid flow path, wherein the liquid chamber is provided with a reference plane which is not deformed by a pressure in the extracorporeal circulating circuit, a deformable plane which is disposed separately from the reference plane and is at least partially deformed by the pressure in the extracorporeal circulating circuit, a first connecting plane which connects the deformable plane with the reference plane to form a closed liquid-tight space therein and is not deformed by a pressure in the extracorporeal circulating circuit, a liquid flow inlet provided in a side surface of the first connecting plane, and a liquid flow outlet which is disposed at a position separated from the liquid flow inlet by a distance from more than one half to less than one of the inner circumference in the direction of a flow of a liquid wherein the liquid is introduced along an inner circumference of side surfaces of the first connecting plane;

wherein the pressure measuring means is disposed outside of the liquid chamber for measuring a deformation quantity of the deformable plane; and wherein the liquid flow path is connected to the liquid flow inlet in a liquid tight manner so that the liquid introduced into the liquid chamber flows along the inner circumference of side surfaces of the first connecting plane.

2. The pressure sensor for an extracorporeal circulating circuit according to claim 1, further comprising a baffle plate wherein the baffle plate is disposed near the first connecting plane to disturb the flow of the liquid.

3. The pressure sensor for an extracorporeal circulating circuit according to claim 1, further comprising an air chamber, wherein the air chamber has an opposing plane which is not deformed by a pressure and is disposed separately from the deformable plane so that the deformable plane is positioned between the reference plane and the opposing plane, a second connecting plane which is not deformed by a pressure and connects the opposing plane with the deformable plane to form a closed air-tight space therein, and an air inlet/outlet which is provided in a side surface of the second connecting plane or the opposing plane; and wherein the pressure measuring means is an air chamber pressure measuring means which is connected to the air inlet/outlet of the air chamber via a communication section.

4. The pressure sensor for an extracorporeal circulating circuit according to claim 3, wherein on the assumption that $V_A$ is volume of the air chamber in the initial state, $P_A$ is pressure in the air chamber in the initial state (where $-200$ mmHg$<P_A<200$ mmHg), $V_L$ is volume of the liquid chamber in the initial state, $V_T$ is volume of the communication section, $P_{MIN}$ is the minimum measurable pressure of the pressure sensor (where $-600$ mmHg$<P_{MIN}<-200$ mmHg), $P_{MAX}$ is the maximum measurable pressure (where 200 mmHg$<P_{MAX}<600$ mmHg), and $P_0$ is atmospheric pressure, $V_A$, $V_L$, and $V_T$ are set to satisfy the following Expressions (1) and (2) (where $P_A$, $P_{MIN}$, and $P_{MAX}$ are expressed as gage pressure, and $P_0$ is expressed as absolute pressure):

$$\{(P_{MAX}+P_0) \div (P_A+P_0)-1\} \times V_T < V_A \quad (1)$$

$$\{(P_A+P_0) \div (P_{MIN}+P_0)-1\} \times (V_A+V_T) < V_L < 10 \text{ mL} \quad (2); \text{ and}$$

the deformable plane has a flat plate shape when the liquid chamber and the air chamber have a pressure $P_0$.

5. The pressure sensor for an extracorporeal circulating circuit according to claim 4, wherein the deformable plane is sandwiched between two containers of the air chamber and the liquid chamber to be mechanically sealed at the peripheral portion thereof; and on the assumption that L is width of the sealing portion of the deformable plane which is sandwiched between the two containers and in contact with the containers (where 0.3 mm$<$L$<$10 mm), ν is a Poisson's ratio of the deformable plane, h is thickness of the deformable plane (where 0.2 mm$<$h$<$3.0 mm), and t is amount of compression of the deformable plane by the mechanical seal (where 0.05$<$t/h$<$0.50), the deformable plane has a flat plate shape by the fact that the liquid chamber and the air chamber have a pressure equal to atmospheric pressure when the deformable plane is mechanically sealed under condition of a tensile displacement λ which satisfies an expression:

$$-\nu \times L \times (t \div h)/2 < \lambda.$$

6. The pressure sensor for an extracorporeal circulating circuit according to claim 4, wherein the deformable plane has a ring section having a thickness larger than that of the deformable plane at the periphery thereof as a sealed portion; and on the assumption that La is width of the sealing portion of the ring section which is sandwiched between the two containers and in contact with the containers (where 0.3 mm$<$La$<$10 mm), νa is a Poisson's ratio of the ring section, and ha is thickness of the ring section (where 1.0 mm$<$ha$<$5.0 mm), and ta is amount of compression of the ring section by the mechanical seal (where 0.05$<$ta/ha$<$0.50), the deformable plane has a flat plate shape by the fact that the liquid chamber and the air chamber have a pressure equal to atmospheric pressure when the deformable plane is mechanically sealed under condition of a tensile displacement λ which satisfies an expression: $-\nu a \times La \times (ta \div ha)/2 < \lambda$.

7. The pressure sensor according to claim 6, wherein the ring section has a circular cross section.

8. The pressure sensor for an extracorporeal circulating circuit according to claim 6, wherein the sealing portion of the air chamber and/or the sealing portion of the liquid chamber is provided with a groove into which the ring section is inserted, and the groove has inner surfaces which are inclined relative to the deformable plane to form an acute angle therebetween.

9. The pressure sensor for an extracorporeal circulating circuit according to claim 4,
wherein the air chamber and the liquid chamber are housed in a common casing, and
wherein the pressure sensor in the extracorporeal circulating circuit further comprises an attachment surface to which the casing is attached, and an attachment sensing means for detecting the attachment of the casing to the attachment surface, wherein the attachment surface is configured to have the communication section with an opening which is connectable to the air inlet/outlet of the air chamber, so that the air inlet/outlet and the communication section are connected to each other in an air tight manner when the attachment sensing means detects attachment of the casing.

10. The pressure sensor for an extracorporeal circulating circuit according to claim 9, wherein the attachment sensing means is attached to the casing.

11. The pressure sensor for an extracorporeal circulating circuit according to claim 9, wherein the attachment sensing means is attached to the attachment surface.

12. The pressure sensor for an extracorporeal circulating circuit according to claim 9, wherein the attachment surface has a cushioning section around the opening of the communication section for applying a force toward the casing, and the cushioning section is movable toward the connection between the air inlet/outlet and the communication section.

13. The pressure sensor for an extracorporeal circulating circuit according to claim 9, wherein the attachment sensing means detects the contact between the casing and the attachment surface when the casing is attached to the attachment surface.

14. The pressure sensor for an extracorporeal circulating circuit according to claim 9, wherein the attachment sensing means detects that the casing is attached to a predetermined position after rotating along the attachment surface.

15. The pressure sensor for an extracorporeal circulating circuit according to claim 9, further comprising a rotating body around the casing, and the attachment sensing means detects that the rotating body is attached to a predetermined position after rotating along the attachment surface.

16. The pressure sensor for an extracorporeal circulating circuit according to claim 4, further comprising:
an air chamber adjusting to atmospheric pressure means for pressurizing the air chamber to atmospheric pressure;
a liquid chamber adjusting to atmospheric pressure means for pressurizing the liquid chamber to atmospheric pressure;
a liquid chamber pressure controlling means for controlling a pressure in the liquid chamber;
a liquid chamber pressure measuring means for measuring a pressure in the liquid chamber; and
a damage detecting means for detecting damage of the deformable plane by changing a pressure in the liquid chamber to measure a pressure in the air chamber corresponding to the pressure in the liquid chamber for comparison.

17. The pressure sensor for an extracorporeal circulating circuit according to claim 16, wherein after the air chamber adjusting to atmospheric pressure means and the liquid chamber adjusting to atmospheric pressure means pressurize the air chamber and the liquid chamber to atmospheric pressure respectively, on the assumption that the pressure in the liquid chamber when the deformable plane closely contacts a wall surface of the air chamber by increasing the pressure in the liquid chamber using the liquid chamber pressure controlling means is P1, the damage detecting means determines that the deformable plane is damaged when the liquid chamber pressure controlling means further increases the pressure in the liquid chamber up to P2 (>P1) and the pressure in the air chamber becomes higher than P1.

18. The pressure sensor for an extracorporeal circulating circuit according to claim 16, wherein after the air chamber adjusting to atmospheric pressure means and the liquid chamber adjusting to atmospheric pressure means pressurize the air chamber and the liquid chamber to atmospheric pressure respectively, on the assumption that the pressure in the liquid chamber when the deformable plane closely contacts a wall surface of the liquid chamber by decreasing the pressure in the liquid chamber using the liquid chamber pressure controlling means is P3, the damage detecting means determines that the deformable plane is damaged when the liquid chamber pressure controlling means further decreases the pressure in the liquid chamber up to P4 (<P3) and the pressure in the air chamber becomes lower than P3.

19. The pressure sensor for an extracorporeal circulating circuit according to claim 16, wherein the damage detecting means memorizes characteristics of a change of a pressure in the air chamber corresponding to a pressure in the liquid chamber in advance; and after the air chamber adjusting to atmospheric pressure means and the liquid chamber adjusting to atmospheric pressure means pressurize the air chamber and the liquid chamber to atmospheric pressure respectively, the liquid chamber pressure controlling means increases or decreases the pressure in the liquid chamber; and then the damage detecting means determines that the deformable plane is damaged when the change of the pressure in the air chamber corresponding to the change of the pressure in the liquid chamber which is measured by the liquid chamber pressure measuring means is different from the characteristics of the change of the pressure in the air chamber which is memorized in advance.

* * * * *